US007081092B2

(12) United States Patent
Schutt

(10) Patent No.: US 7,081,092 B2
(45) Date of Patent: Jul. 25, 2006

(54) METHODS AND APPARATUS FOR MONITORING AND QUANTIFYING THE MOVEMENT OF FLUID

(75) Inventor: Ernest G. Schutt, San Diego, CA (US)

(73) Assignee: IMCOR Pharmaceutical Company, San Diego, CA (US)

( * ) Notice: Subject to any disclaimer, the term of this patent is extended or adjusted under 35 U.S.C. 154(b) by 90 days.

(21) Appl. No.: 10/962,958

(22) Filed: Oct. 12, 2004

(65) Prior Publication Data
US 2005/0049484 A1 Mar. 3, 2005

Related U.S. Application Data

(63) Continuation of application No. 10/444,424, filed on May 23, 2003, now Pat. No. 6,802,813, which is a continuation of application No. 09/966,016, filed on Sep. 27, 2001, now abandoned, which is a continuation of application No. 09/451,212, filed on Nov. 29, 1999, now abandoned, which is a continuation of application No. PCT/US98/10944, filed on May 29, 1998, which is a continuation of application No. 10/267,352, filed on Oct. 9, 2002, which is a continuation of application No. 09/523,872, filed on Mar. 13, 2000, now abandoned, which is a continuation of application No. 09/092,351, filed on Jun. 5, 1998, now Pat. No. 6,056,943, which is a continuation of application No. 08/884,542, filed on Jun. 27, 1997, now Pat. No. 6,019,960, which is a continuation of application No. 08/688,167, filed on Jul. 29, 1996, now Pat. No. 5,733,527, which is a continuation of application No. 08/314,074, filed on Sep. 28, 1994, now Pat. No. 5,540,909.

(60) Provisional application No. 60/048,041, filed on May 30, 1997.

(51) Int. Cl.
A61B 8/14 (2006.01)

(52) U.S. Cl. .................................... 600/458

(58) Field of Classification Search ........ 600/437–472; 73/625, 626; 128/916; 424/9.51, 9.52
See application file for complete search history.

(56) References Cited

U.S. PATENT DOCUMENTS

| 4,466,442 A | 8/1984 | Hilmann et al. |
| 4,572,203 A | 2/1986 | Feinstein |
| 4,657,756 A | 4/1987 | Rasor et al. |
| 4,675,173 A | 6/1987 | Widder |
| 4,684,479 A | 8/1987 | D'Arrigo |
| 4,718,433 A | 1/1988 | Feinstein |
| 4,844,882 A | 7/1989 | Widder et al. |
| 4,849,210 A | 7/1989 | Widder |
| 4,951,673 A | 8/1990 | Long |
| 4,957,656 A | 9/1990 | Cerny et al. |
| 5,088,499 A | 2/1992 | Unger |
| 5,116,599 A | 5/1992 | Rogers et al. |
| 5,123,414 A | 6/1992 | Unger |
| 5,141,738 A | 8/1992 | Rasor et al. |
| 5,143,715 A | 9/1992 | Barnhart |
| 5,250,283 A | 10/1993 | Barnhart |
| 5,271,928 A | 12/1993 | Schneider et al. |
| 5,315,997 A | 5/1994 | Widder et al. |
| 5,393,524 A | 2/1995 | Quay |
| 5,401,493 A | 3/1995 | Lohrmann et al. |
| 5,409,688 A | 4/1995 | Quay |
| 5,531,980 A | 7/1996 | Schneider et al. |
| 5,536,489 A | 7/1996 | Lohrmann et al. |
| 5,540,909 A | 7/1996 | Schutt |
| 5,552,133 A | 9/1996 | Lambert et al. |
| 5,556,610 A | 9/1996 | Yan et al. |
| 5,558,092 A | 9/1996 | Unger et al. |
| 5,558,094 A | 9/1996 | Quay |
| 5,558,853 A | 9/1996 | Quay |
| 5,558,854 A | 9/1996 | Quay |
| 5,558,855 A | 9/1996 | Quay |
| 5,558,856 A | 9/1996 | Klaveness et al. |
| 5,562,893 A | 10/1996 | Lohrmann |
| 5,567,413 A | 10/1996 | Klaveness et al. |
| 5,573,751 A | 11/1996 | Quay |
| 5,578,292 A | 11/1996 | Schneider et al. |
| 5,595,723 A | 1/1997 | Quay |
| 5,605,673 A | 2/1997 | Schutt |
| 5,685,310 A | 11/1997 | Porter |
| 5,707,607 A | 1/1998 | Quay |
| 5,735,281 A | 4/1998 | Rafter et al. |

(Continued)

FOREIGN PATENT DOCUMENTS

EP 0359246 3/1990

(Continued)

OTHER PUBLICATIONS

Rodriquez et al *Capacity of Human Coronary Arteries A Post Morten Study* Circulation 19, pp 570-578 (Apr. 1959).

(Continued)

Primary Examiner—Ali Imam
(74) Attorney, Agent, or Firm—Gerard P. Norton; Norton & Diehl LLC

(57) ABSTRACT

Methods, systems and devices are provided for monitoring and quantifying the movement of fluid in a target region. Generally, an imaging agent is introduced into a target region through fluid flow. The imaging agent in the target region is then disrupted using appropriate methods such as the application of ultrasonic energy. As fluid flow brings undisrupted imaging agent into the target region, the rate of accumulation is monitored and quantified thereby providing the exchange rate and flow rate of the fluid in the target region. The disclosed invention is particularly useful for medical applications such as determining the flow rate of blood in an organ or tissue.

20 Claims, No Drawings

U.S. PATENT DOCUMENTS

| | | | |
|---|---|---|---|
| 5,776,429 A | 7/1998 | Unger et al. | 424/9.52 |
| 5,833,613 A | 11/1998 | Averkiou et al. | 600/440 |
| 6,186,951 B1 | 2/2001 | Lizzi et al. | 600/458 |
| 6,312,383 B1 | 11/2001 | Lizzi et al. | 600/437 |
| 6,315,730 B1 | 11/2001 | Hoff et al. | 600/458 |
| 6,802,813 B1 * | 10/2004 | Schutt | 600/454 |

FOREIGN PATENT DOCUMENTS

| | | |
|---|---|---|
| EP | 0713680 A2 | 5/1996 |
| EP | 0770352 A1 | 5/1997 |
| WO | 9115999 | 10/1991 |
| WO | 9416739 | 8/1994 |
| WO | 9501187 | 1/1995 |
| WO | 9503835 | 2/1995 |
| WO | 9640278 | 12/1996 |
| WO | 9640282 | 12/1996 |

OTHER PUBLICATIONS

Wei K. et al *Quantification of Myocardial Blood Flow with Ultrasound-Induced Destruction of Microbubbles Administered as a Constant Venous Infusion* Circulation 97 (5) pp 473-483 (Feb. 10, 1998) XP002077428.

Wei K. et al. *Use of Microbubble Destruction as a Novel Approach for Quantification of Myocardial Perfusion with Contrast Echocardiography During Venous Infusion of Contrast* J. of The American College of Cardiology 29 (2, Suppl. A) (Feb. 1997) XP002077429.

Jong De N *Improvements in Ultrasound Contrast Agents* IEEE Engineering in Medicine and Biology Magazine 15(6) pp 72-82 (Nov. 1996) XP000638030.

* cited by examiner

METHODS AND APPARATUS FOR MONITORING AND QUANTIFYING THE MOVEMENT OF FLUID

RELATED APPLICATIONS

This application is a continuation of U.S. patent application Ser. No. 10/444,424, now PAT 6,802,813, filed 23 May 2003, which is a continuation of U.S. Ser. No. 09/966,016 filed 27 Sep. 2001, now abandoned, which is a continuation of 09/451,212 filed 29 Nov. 1999, now abandoned, which is a continuation of PCT Application No. PCT/US98/10944 filed 29 May 1998, which PCT Application claims priority to U.S. Provisional Application No. 60/048,041 filed 30 May 1997. This application is also a continuation of U.S. Ser. No. 10/267,352 filed on 9 Oct. 2002, which is a continuation of U.S. patent application Ser. No. 09/523,872 filed on 13 Mar. 2000, now abandoned, which is a-continuation of U.S. patent application Ser. No. 09/092,351, filed on 5 Jun. 1998, now U.S. Pat. No. 6,056,943, which is a continuation of U.S. patent application Ser. No. 08/884,542, filed on 27 Jun. 1997, now U.S. Pat. No. 6,019,960, which is a continuation of U.S. patent application Ser. No. 08/688,167, filed on 29 Jul. 1996, now U.S. Pat. No. 5,733,527, which is a continuation of U.S. patent application Ser. No. 08/314,074, filed on 28 Sep. 1994, now U.S. Pat. No. 5,540,909.

FIELD OF THE INVENTION

In a broad aspect, the present invention relates to methods and systems for monitoring and quantifying the movement of fluid in a target region. More particularly, the present invention is directed to methods and systems that allow for determination of the rate of fluid movement through a target region including those that comprise tissue or a vascular array.

BACKGROUND OF THE INVENTION

Modern imaging techniques are rapidly improving the diagnostic accuracy and clinical management of pathological disorders. Among the more prevalent imaging technologies currently available are ultrasound, magnetic resonance imaging (MRI), computerized tomography (CT), and positron emission tomography (PET). Radiographic procedures, such as computed tomography and positron emission tomography, operate by detecting and mapping differences in the composition of a target object. Unfortunately CT and PET utilize ionizing radiation and require relatively expensive equipment. Conversely, MRI and ultrasound do not require ionizing radiation and, at least in the case of ultrasound imaging, utilize relatively inexpensive equipment.

In magnetic resonance visualization, advantage is taken of the fact that some atomic nuclei, such as, for example, hydrogen nuclei or fluorine nuclei have both nuclear spin and nuclear magnetic moment, and therefore can be manipulated by applied magnetic fields. Traditional MRI comprises the use of a magnetic field that is established across a body to align the spin axes of the nuclei of a particular chemical element in the direction of the magnetic field. The aligned, spinning nuclei execute precessional motions around the aligning direction of the magnetic field. For the aligned, spinning nuclei the frequency at which they precess around the direction of the magnetic field is a function of the particular nucleus which is involved and the magnetic field strength. The selectivity of this precessional frequency with respect to the strength of the applied magnetic field is very sharp and this precessional frequency is considered a resonant frequency.

After alignment or polarization of the selected nuclei, a burst of radio frequency energy at the resonant frequency is radiated at the target body to produce a coherent deflection of the nuclei spin alignment. When the deflecting radio energy is terminated, the deflected or disturbed spin axes are reoriented or realigned, and in this process radiate a characteristic radio frequency signal which can be detected by an external coil and then resolved by the MRI system to establish image contrast between different types of tissue in the body.

Contrast agents for MRI must possess a substantially different concentration of the nuclei used as a basis for scanning. For example, in a hydrogen scanning system, an agent substantially lacking hydrogen can be used. Conversely, in a magnetic visualization system that scans for a physiologically minor nucleus such as the fluorine nuclei, a substance with a high concentration of that nucleus would provide the appropriate contrast.

Imaging or contrast agents may be introduced into the body space in various ways depending on the imaging requirement. In the form of liquid suspensions or emulsions they may be placed into the area of interest by oral ingestion or injection into the bodily space (either directly or by channeling through selected vessels). Typically, the contrast agents are transported by the blood or other fluids to the regions of interest. A suitable contrast agent must be biocompatible, that is non-toxic and chemically stable, not absorbed by the body or reactive with the tissue, and eliminated from the body within a short time.

In ultrasound imaging, ultrasonic waves are transmitted into an object or patient via a transducer. As the sound waves propagate through the object or body, they are either reflected or absorbed by tissues and fluids. Reflected ultrasonic waves are then received by the transducer and converted into electrical signals from which an image is generated. The acoustic properties of the tissues and fluids determine the contrast which appears in the resulting image.

Ultrasound imaging, therefore, makes use of differences in tissue density and composition that affect the reflection of sound waves by those tissues. Images are especially sharp where there are distinct variations in tissue density or compressibility, such as at tissue interfaces. Interfaces between solid tissues, the skeletal system, and various organs and/or tumors are readily imaged with ultrasound.

Accordingly, in many imaging applications ultrasound performs suitably without use of contrast enhancement agents; however, for other applications, such as visualization of flowing blood in tissues, there have been ongoing efforts to develop agents to provide contrast enhancement. One particularly significant application for these contrast agents is in the area of vascular imaging. Such ultrasound contrast agents can improve imaging of flowing blood in the brain, heart, kidneys, lungs, and other tissues. This, in turn, facilitates research, diagnosis, surgery, and therapy related to the imaged tissues. A blood pool contrast agent also allows imaging on the basis of blood content (e.g., tumors and inflamed tissues) and can aid in the visualization of the placenta and fetus by enhancing only the maternal circulation.

In this regard, a variety of ultrasound contrast enhancement agents have been proposed. The most successful agents generally consist of microbubbles that can be injected intravenously. In their simplest embodiment, microbubbles are miniature bubbles containing a gas, such as air, and are formed through the use of foaming agents, surfactants or other film forming agents, or encapsulating agents. More advanced formulations of microbubbles, such as those described in U.S. Pat. No. 5,605,673, comprise fluorochemical gases or vapors. In any event, the microbubbles provide a physical object in the flowing blood that is of a different density and possesses a much higher compressibility than the surrounding fluid tissue and blood. As a result, these microbubbles act as good reflectors of ultrasound energy and can easily be imaged.

While contrast agents for both ultrasound and magnetic visualization can substantially enhance the resolution of physiological structures and highlight deficiencies in blood flow through tissue, their use has not, at least prior to the instant application, allowed for the reliable quantitative assessment of blood flow. For example, prior to the instant invention, common ways of determining the rate of blood flow included Doppler ultrasound or by introduction of a bolus of an imagable contrast agent into a coronary artery through a catheter and measurement of the transit time of the bolus through the heart. Unfortunately, Doppler measurements of vascular flow have not proven efficient enough to provide the necessary accuracy in clinical situations. Conversely, although more accurate, the introduction of a bolus of contrast agent into a coronary artery may lead to complications. Moreover, as the technique requires placement of a catheter directly into the coronary artery, it is extremely invasive. This substantially increases patient discomfort, burden on hospital resources and precludes the use of the procedure on all but the most serious cases. Perhaps most importantly, while the aforementioned techniques may be used to give a rough estimate of blood flow through the heart or in a major artery, current procedures are unable to accurately quantitate the rate of blood flow or perfusion within a particular tissue; i.e. within the liver, kidney or heart.

Accordingly, it is an object of the present invention to provide methods for the accurate determination for the rate or amount of blood flow through a particular target region as a factor of time.

It is another object of the present invention to provide for the accurate measurement of the perfusion rate of a selected target tissue.

It is still another object of the present invention to accurately provide for the noninvasive determination of blood flow through the heart.

It is yet another object of the present invention to provide for the accurate measurement of rate of fluid flow using ultrasound imaging or magnetic visualization techniques.

SUMMARY OF THE INVENTION

These and other objects are accomplished by the methods and systems of the present invention which, in a broad sense, provide for the accurate monitoring and/or measurement of fluid flow or perfusion in a selected structure. Preferably the structure is biological in nature and comprises a vascular or microvascular system. More preferably, the structure is a selected target region comprising tissue or at least a portion of an organ such as a kidney, liver, brain or heart. In such cases, the measured flow may comprise the flow of fluid through the structure (i.e. blood flow through the heart) or may comprise the rate of perfusion of a target region (i.e. permeation of an organ or tissue with blood). Moreover, the present invention provides for the determination of the selected values through relatively non-invasive means. Accordingly, the disclosed methods and systems may be used to safely monitor and/or diagnose physiological conditions.

Generally, the invention provides the desired data by observing the influx of imaging agent into the target region over a period of time. In preferred embodiments the present invention determines selected values, such as perfusion or flow rate (i.e. flow of fluid per unit volume per unit time), by eliminating or reducing a signal from an area of interest (target region) and subsequently detecting a return of the signal over a period of time. This general technique may also be used to provide the fluid exchange rate (i.e. fraction of fluid exchanged per unit time). The observed signal (or signal level) is associated with a contrast or imaging agent and increases in intensity as a function of agent concentration in a given target region. Preferably, the signal associated with the contrast or imaging agent may be reduced or eliminated by exposing the selected region to the appropriate form of energy including ultrasonic energy or magnetic pulses. Conversely, the signal may be enhanced or otherwise measurably altered through the application of energy or change in the applied magnetic field. Most commonly, agents compatible with the present invention will be associated with magnetic resonance visualization or ultrasound imaging although agents used in computerized tomography or positron emission tomography may also be compatible if they exhibit the necessary signal attenuation following exposure to the appropriate form of energy. In this respect, it will be appreciated that any contrast or imaging agent which exhibits a reduced signal following exposure to the selected form of energy is suitable for use with the present invention.

In any event, the present invention further provides a method for determining an exchange rate for a moving fluid in a target region comprising the steps of:

a. introducing undisrupted imaging agent into a moving fluid, said moving fluid being present in a target region;

b. allowing undisrupted imaging agent to penetrate said target region;

c. disrupting the imaging agent in the target region to provide disrupted imaging agent having a signal level less than that provided by undisrupted imaging agent;

d. allowing the moving fluid to transport undisrupted imaging agent from outside the target region into the target region;

e. interrogating the target region with a monitor capable of registering the signal level whereby an increase in signal level corresponding to an increase in undisrupted imaging agent is observed; and f. calculating the exchange rate of moving fluid in the target region based on the observed increase in signal level.

It should be appreciated that, although the present invention will most often be described in terms of reducing the generated signal from the target region, it is not limited to such embodiments. That is, employment of ultrasound techniques will typically result in the disruption of the contrast agent and reduction of the signal in the target region. In contrast, magnetic resonance techniques may be used to enhance, reduce or otherwise measurably alter the amount and signature of the signal generated depending on the applied field and orientation of the agent nuclear spin. Accordingly, the present invention is not limited to the reduction and subsequent reappearance of generated signal in the target region but rather encompasses any measurable alteration of the signal in the target region and subsequent "renormaliztion" of the signal.

Another embodiment of the invention comprises a method for determining the rate of fluid exchange in a target region of a patient comprising:

a. introducing intact signal-generating contrast agent into a bodily fluid that moves into a target region such that the contrast agent is transported by said fluid into said target region;
 b. rendering said contrast agent which is present in said target region at least partially disrupted;
 c. thereafter allowing additional intact contrast agent to be carried into said target region by said bodily fluid; and
 d. calculating the rate of fluid exchange in the target region based on the rate at which intact contrast agent enters the target region.

In particularly preferred embodiments, the signal generating moiety will comprise an ultrasound contrast agent such as a microbubble which is capable of being disrupted or destroyed by exposure to ultrasound energy. In other preferred embodiments, a magnetic resonance imaging agent may be employed. Using techniques well known to those skilled in the art, the selected imaging agent is introduced into the object or body to be imaged and allowed to permeate or perfuse the region of interest. Following introduction the region of interest, or target region, is exposed to ultrasonic, magnetic or other appropriate energy. The amount of power and length of exposure will depend on a number of factors but, when taken together, should be sufficient to reduce, enhance (i.e. in MRI) or otherwise measurably alter the signal received from the imaging agent in the target region upon subsequent interrogation. With regard to microbubbles, exposure to enough ultrasound energy will disrupt or destroy them, thereby reducing or eliminating the signal provided by the imaging agent. In any event, following disruption (or other alteration) of the generated signal, the target region will initially provide relatively little contrast, or measurably different contrast, when subsequently interrogated using conventional techniques.

After alteration or reduction of the signal in the target region, blood or other fluids gradually perfuse into, or flow through, the area of altered contrast bringing with them (i.e. transporting) undisrupted imaging agent. It is important to emphasize that the reduction of signal by exposure to ultrasound energy is a localized effect and that surrounding tissue and fluids still comprise sufficient levels of undisrupted contrast agent to essentially provide a full strength signal upon interrogation. Accordingly, as blood or fluids enter the target region, the localized concentration of contrast agent gradually increases thereby providing a stronger signal over time. Observing and measuring the relative increase in signal strength over selected periods allows for determination of the rate of fluid flow or perfusion and, consequently, quantification of the volumetric blood flow in a selected target region.

Observation of the increasing signal strength and determination of the desired values may be accomplished using conventional interrogation techniques such as ultrasound or magnetic resonance visualization. It will be appreciated that each interrogation of the target region may be used to produce a single snapshot or "frame" of the area of interest. Preferably, the initial interrogation of the target region occurs concurrently with or following disruption of the imaging agent and prior to the introduction of any new, undisrupted imaging agent from the surrounding area. This original or "baseline" frame records all the tissue and transducer artifacts and may be subtracted, digitally or otherwise, from subsequent interrogative frames (each produced by a discrete interrogation) to isolate changes in signal strength and increase the sensitivity of the measurements.

Those skilled in the art will appreciate that the interrogation of the target region may be performed at any desirable interval or intervals and may occur as often as necessary to produce an accurate measurement of fluid flow. In a preferred embodiment, localized disruption of the imaging agent is accomplished prior to each separate interrogation. That is, the imaging agent in the target region is disrupted by the application of power and, after a preselected interval, the area is interrogated using a compatible detection method. During, or immediately after, collection of the appropriate data, the imaging agent in the target region may be disrupted again to where the signal strength is approximately the same as it was in the baseline frame. In one embodiment, the image may be continuously disrupted with a pause of a selected interval prior to interrogation and return to the disrupted state. Alternatively, the target region is left undisturbed for a period sufficient to allow the local concentration of contrast agent and signal strength to return to partial or full predisruption levels. In either case the cycle or process (disruption and interrogation) may then be repeated using the same or different preselected interval subsequent to disruption and prior to interrogation. Within this embodiment it is immaterial that the imaging agent is disrupted during the interrogation step as the entire system to be imaged is to be "reset" i.e. by disrupting the imaging agent (and signal level) prior to any subsequent measurement. As previously alluded to, the interrogation step may actually comprise the disruption step (or the initial frame of the disruption step) in preferred embodiments. For such embodiments, the operator may advantageously use the same power settings for both the disruption and interrogation steps.

Accordingly, another embodiment of the invention comprises a method for determining the exchange rate of blood in a target region comprising the steps of:

a. introducing a microbubble contrast agent into moving blood of a mammal;
 b. allowing the moving blood to transport said microbubble contrast agent to a preselected target region in said mammal;
 c. applying localized ultrasonic power to said target region to disrupt at least a portion of the microbubble contrast agent therein;
 d. interrogating the target region with an ultrasound scanner to provide a baseline frame representative of the localized signal level;
 e. allowing the moving blood to transport undisrupted microbubble contrast agent into said target region whereby the signal level therein is increased;
 f. subsequently interrogating the target region with an ultrasound scanner to provide at least one interrogative frame representative of the localized signal level; and
 g. processing said baseline frame and said interrogative frame to calculate the rate of blood exchange based on the increase in target region signal level.

In another preferred embodiment, multiple interrogation steps may be performed sequentially to generate a plurality of interrogative frames without intervening disruption steps. However, when measurements are made using such procedures, it is preferable that the interrogations do not substantially disrupt the localized imaging agent or unduly reduce the signal strength. Accordingly, in such procedures the interrogation steps are typically carried out at lower power than the initial disruption step. While multiple interrogation methods may require intermittent adjustment of power levels and corresponding image reception scales, i.e. gray scale contrast in ultrasound, the procedure allows for more rapid acquisition of data and potentially more accurate measurements due to the number of sequential frames that may quickly be collected at varying intervals.

For example, when ultrasound imaging agents comprising microbubbles are used in the present invention an initial burst of approximately one second (at 60 frames per second) could be used to disrupt the bubbles in the target region. The last frame of this burst could be observed and used as a baseline frame where the amount of received signal is equated to zero. Note that this is a relative value and the absolute level of signal received is relatively immaterial for the purposes of the invention. The region of interest could then be interrogated using ultrasound after a short period, i.e. 0.2 seconds, with the received signal used to produce a discrete interrogation or interrogative frame. It will be appreciated that the primary detectable difference between the frame produced at 0.2 seconds and the baseline frame will be the signal generated by imaging agent that has flowed into the target region with blood or other fluids. Subtraction of the baseline image from the subsequent interrogative frame provides an easily quantifiable signal that is proportional to the amount imaging agent in the region of interest. This collected data may be used to calculate the desired values or could be combined with other derived measurements at the same or different preselected intervals to provide increasingly accurate flow or perfusion rates.

The selected values may be derived using as little as one interrogation frame. However, as described above, additional optional data may be collected by repeating the procedure with intervening localized disruption of the imaging agent or simply by sequentially producing multiple interrogation frames at substantially non-disrupting power. In the case of the former, the imaging agent in the target region would be disrupted to signal levels approximating that of the original baseline frame prior to subsequent interrogation. Of course a new baseline frame could be produced for each cycle and used in subsequent calculations with the respective interrogative frame. Disruption could occur during, or immediately following, the previous interrogation or after a period of time. Preferably the ultimate or maximum signal strength remains similar, i.e. within 10%, 20%, or 50% of the signal strength immediately prior to the initial disruption, during data collection. Following the second disruption, a second interrogation frame could be generated at the same interval (i.e. 0.2 seconds) or at any other interval (i.e. 0.5 seconds). Whatever interval is selected, the amount of signal strength may be determined by subtracting out the first or second baseline frame (which should be roughly equivalent if the same disruptive forces were used) from the second interrogation frame. That is, the original baseline frame could be subtracted from each interrogation frame despite the intervening disruption or, each baseline frame immediately proceeding the interrogative-frame could be used to provide the relative signal level. In any case, this process or cycle of intervening disruption and interrogation may be performed as many times as desired while the imaging agent is present in sufficient quantity to produce a readable signal.

Alternatively, additional discrete interrogative frames could be produced in a like manner at selected intervals such as at 0.25 seconds, 0.5 seconds, 1.0 second, 2.0 seconds, 3.0 seconds, etc. after the first baseline frame. Of course, interrogation of the target region could also be conducted on an essentially continuous basis or with extremely short intervals (i.e. on the order of 100 frames per second) between signal level observation and the production of discrete frames. Essentially, the interrogation and signal measurement of the target region may be conducted at any desired interval or intervals. No intervening disruption of the imaging agent in the target region is undertaken. Accordingly, these interrogations preferably occur under conditions that do not substantially disrupt the imaging agent in the target region. For example, they may be conducted at lower power than the disruption event or for shorter intervals. As such, the strength of the received signals will be cumulative, i.e. the reading at 1.0 second will be greater than that received at 0.5 seconds due to the increase in imaging agent concentration during the intervening period.

Regardless of how the interrogative frames are generated, the target region is eventually interrogated at a point when the signal strength is approximately equivalent to what it was prior to the initial disruption of the agent, i.e. at 15 or 30 seconds to provide a "maximum signal" frame. Those skilled in the art will appreciate that this maximum signal frame is not necessary to calculate the desired values (i.e. when using an exponential fit) and is therefore optional with regard to the invention. Of course, this maximum signal frame could also be derived prior to the initial disruption of imaging agent. In any case, knowing the relative signal strengths of the baseline frame (0%), maximum signal frame (100%) and intervening time point frames (interrogative frames), the rate of signal replacement (and hence the exchange rate and perfusion rate into the target region) may be easily determined using interpolation or other conventional mathematical techniques.

More particularly, the increase in signal per unit time divided by the strength of the signal in the maximum signal frame gives the volumetric fraction of a fluid (typically blood, plasma etc.) flowing through the tissue or organ (i.e. the fluid exchange rate). Knowing this rate, one can easily and accurately calculate the inverse of the average time it takes to replace all the fluid in the target region. This exchange rate, when multiplied by the fluid content of the tissue in the target region (easily derived from the literature or direct measurement) provides the perfusion rate (or flow rate) which is defined as milliliters of fluid flow per second per cubic centimeter of tissue. For the purposes of the present disclosure the term "flow rate" shall be held to be equivalent to the term "perfusion rate" and will be used interchangeably unless the context dictates otherwise. The fluid content of the tissue may further be derived by dividing the net signal level of the tissue by the signal level provided by a fast moving pure blood adjacent to the tissue i.e. a main vein or artery.

As previously indicated, it will be appreciated that any imaging or contrast agent capable of disruption by the application of energy is compatible with the present invention. Particularly preferred are ultrasound contrast agents comprising microbubbles or microballoons including those microbubbles comprising fluorinated gases or vapors. Such microbubbles may be, for example, in the form of free gas microbubbles, microbubbles encapsulated by relatively insoluble microspheres, microbubbles comprising a surfactant or tenside membrane, microbubbles formed by local supersaturation and microbubbles stabilized by liposomes or viscosity enhancing solutions. Similarly, imaging agents used for magnetic resonance visualization are also preferred for use in the present invention. Such imaging agents may typically be disrupted or inactivated by the application of bursts of magnetic energy which may alter the local environment of the imagable protons. Following disruption fluid flow may be measured by monitoring the reinfusion of active imaging agent using conventional magnetic visualization techniques.

Accordingly, in another aspect the present inventions comprises the use of fluorinated gases or vapors for the manufacture of a medicament. In particular, the invention comprises use of a fluorinated gas or vapor for the manufacture of a signal-generating contrast agent for determining the rate of fluid exchange in a target region of a patient whereby intact contrast agent is introduced into a flowing bodily fluid such that it is transported into the target region where the contrast agent is at least partially disrupted by the application of energy thereby allowing for calculation of the fluid exchange rate based on the observed rate at which intact contrast agent reinfuses the target region.

Using the aforementioned procedures and contrast agents the present invention allows determination of the rate and amount of blood flow in a target region or tissue, such as heart, brain, myocardium, liver, kidneys, lungs, and other tissue. Such information may be useful in locating and identifying stenotic arteries. Additionally, the present invention may be used to locate and identify dead or necrotic tissue, such as that resulting from heart attacks, strokes, or tissue rejection, since such necrotic tissue exhibits reduced blood flow rates.

Alternatively, the rate of blood flow may be used to locate and identify tissues having increased blood flow rates, such as certain regions of tumors or inflamed tissues. It will be appreciated therefore that the disclosed methods may be used for the detection, identification and classification of neoplasms. The present invention may also be used to measure the blood flow rate in the heart and its tissues during stress or exercise tests. Similarly, blood flow rates in myocardial tissue may be measured after oral or venous administration of drugs designed to increase the blood flow to a tissue. Also, changes in blood flow rates in myocardial tissue due to or during various interventions, such as coronary tissue vein grafting, coronary angioplasty, or use of thrombolytic agents (TPA or streptokinase) can also be measured. Blood flow rates may also be determined throughout the entire circulatory system, to assist in the diagnosis of general vascular pathologies and the viability of placental tissue.

The embodiments of the present method which utilize ultrasound as a detection technique include several beneficial features. For example, no knowledge of the transducer power is necessary to derive the perfusion rate. Furthermore, tissue attenuation and artifacts are eliminated from the signal. In addition, the rate of perfusion may be calculated without knowledge of the microbubble concentration, reflectivity, or power susceptibility. Finally, the present methods permit rapid and automatic calculation of the blood flow rate and tissue perfusion rate.

In addition to the aforementioned methods, the present invention further provides a systems for the determination of fluid exchange rates and perfusion rates. More specifically, one embodiment of the invention comprises a system for determining the rate of fluid exchange in a target region comprising:
  a signal-generating ultrasound contrast agent;
  an ultrasonic transducer capable of non-invasively disrupting at least a portion of the contrast agent present in a target region and observing a signal produced by the contrast agent upon insonation; and
  a processor whereby said processor calculates the rate of fluid exchange in a target region based on transducer observed localized increases in contrast agent signal level following transducer mediated disruption of the contrast agent in the target region.

Of course, it will be appreciated that the disclosed systems are particularly useful for practicing the methods as described herein.

The present invention further provides devices which may be used to determine the fluid exchange rate and perfusion rate of selected target regions. In particular, the invention provides devices for non-invasively determining the rate of fluid exchange in a target region comprising:
  an ultrasonic transducer capable of non-invasively disrupting at least a portion of an ultrasound contrast agent present in a target region and observing a signal produced by the contrast agent upon insonation to provide a plurality of ultrasound images;
  a digital storage medium operably associated with said ultrasonic transducer wherein said digital storage medium receives data representative of said plurality of ultrasound images from the transducer; and
  a processor operably associated with the digital storage medium whereby said processor calculates the rate of fluid exchange in the target region based on measurable differences in the ultrasound image data obtained from the digital storage medium.

With regard to the above-described devices, systems and methods it should be emphasized that the present invention is not limited to the determination of fluid flow rates in biological systems but may be applied to the determination of flow rates in non-biological systems as well. In addition, it should also be emphasized that imaging techniques other than ultrasound may also be utilized in conjunction with the present invention.

Other objects, features and advantages of the present invention will be apparent to those skilled in the art from a consideration of the following detailed description of preferred exemplary embodiments thereof.

DETAILED DESCRIPTION OF THE INVENTION

While the present invention may be embodied in many different forms, disclosed herein are specific illustrative embodiments thereof that exemplify the principles of the invention. It should be emphasized that the present invention is not limited to the specific embodiments illustrated.

Those skilled in the art will appreciate that while the present invention is particularly suited for the determination of blood flow rates and the rate of tissue perfusion it is equally applicable to the determination of the flow rates of other fluids as well. For example, it may be used to measure the movement of fluid in the lymph system or the movement of fluid in the spinal column. Further, the present invention is entirely compatible for monitoring and measuring the movement of fluid in non-biological systems such as pipes or hydraulic systems.

In any event, when using the invention in a biological system a contrast or imaging agent is introduced into fluids passing through or permeating the target region or tissue. The imaging agent is subsequently transported into the target region or tissue. As described previously, the imaging agent present within the target region or tissue is disrupted to the extent that its ability to produce a detectable signal upon subsequent interrogation is, at least partially, impaired. The localized disruption does not substantially impact the ability of the imaging agent outside the target region to produce a detectable signal. Nondisrupted or intact contrast agent is transported into the target region with the flowing or circulating fluid and, as it is detected, allows for the determination of flow rate of the fluid and perfusion rate through the target region. In preferred embodiments, the present invention can be used to directly calculate the rate of blood flow in a selected vein or artery, or calculate the rate of perfusion in a volume of tissue permeated by a microvascular lattice.

It will further be appreciated that the method may be performed with a wide variety of contrast agents using a number of detection procedures. As used herein, the terms "contrast agent" and "imaging agent" are used interchangeably and broadly encompass any compound, composition or formulation that enhances, contrasts or improves the visualization or detection of an object or system in any way. Those skilled in the art will recognize that a large number of suitable contrast or imaging agents have been described in the literature or are commercially available. As long as they meet the criteria set forth herein, any of these agents are compatible with the disclosed invention.

In this regard, any contrast agent which can be selectively rendered less detectable within a target region by exposure to a particular treatment or energy may be employed in the present invention. Moreover, the selected contrast agent may be imaged using other than traditional detection procedures. For example, microbubbles that are traditionally used in conjunction with ultrasound detection methods may, in the context of the present invention, be used with magnetic resonance visualization methods. That is, the microbubble contrast agent may be disrupted using ultrasonic energy and the infusion of intact, detectable microbubbles monitored through magnetic resonance. While any imaging agent possessing the requisite properties may be employed, preferred embodiments of the invention comprise the use of ultrasound contrast agents or magnetic resonance imaging agents.

With regard to these preferred embodiments, it will be appreciated that the present invention may be practiced with a wide variety of microbubble formulations or compositions. Any microbubble formulation which is capable of disruption using ultrasonic energy may be used in the present invention. In especially preferred embodiments the microbubbles are capable of disruption using ultrasonic pulses in the diagnostic or imaging power range.

Preferably, the microbubbles persist for a sufficient amount of time following administration to allow measurements of the rate of increase in microbubble levels in the target region and the determination of maximum signal strength. In this respect preferred microbubble imaging agents have a half life of at least about 1 minute following administration. More preferably the microbubble imaging agents have a half life of at least about 2, 3, 5, or 10 minutes following administration. However, those skilled in the art will appreciate that the disclosed invention may be practiced by continuous intravenous administration of an imaging agent comprising microbubble having any half life including those with half lives on the order of seconds or tens of seconds.

In one preferred embodiment, the microbubbles are adapted to return a signal at a frequency different from the frequency of the ultrasonic pulse emitted by the transducer, such as a harmonic frequency of the ultrasonic pulse. That is, the bubbles are adapted for harmonic imaging such as is described in U.S. Pat. No. 5,540,909 which is incorporated herein by reference. In other preferred embodiments, the microbubbles are adapted to have a relatively long lifetime following administration. Yet, it must be emphasized that, while the present invention may often be described in the context of the preferred embodiments, the instant disclosure is not limited to the use of such microbubble formulations. Rather, as indicated above the present invention is compatible with any imaging or contrast agent, including those useful for ultrasound or magnetic visualization (i.e. MRI), that may be selectively disrupted by the application of energy or the alteration of the magnetic field. It further must be emphasized that any interrogation technique including, but not limited to, ultrasound or magnetic visualization procedures may be used with the disclosed invention as long as it provides for the detection of the selected imaging agent. Significantly, the disruption phase and interrogation phase may incorporate different imaging techniques.

Those skilled in the art will further appreciate that the selected imaging agent may be introduced using any method that provides the desired signal in the target region. For example, the contrast agent may be delivered intraarterially, intravenously, topically, subcutaneously, intramuscularly, intraperitoneally, nasally, pulmonarily, vaginally, rectally, aurally, orally or ocularly depending on the agent selected and the target region. As previously alluded to, the imaging agent may be administered as a bolus or over an extended period such as through an I.V. drip. For example, quantitation of blood flow through the heart or determination of the perfusion rate of an organ may comprise the intravenous administration of an ultrasound microbubble imaging agent. Conversely, observation of fluid dynamics in the gastrointestinal tract may be most effectively achieved by the oral or rectal administration of a magnetic resonance imaging agent. In the case of the exemplary embodiment comprising determination of the perfusion rate of organ tissue, the microbubble contrast agent is preferably administered intravenously and allowed to circulate throughout the body.

After the target region is perfused with a detectable level of imaging agent, the microbubbles may be disrupted as disclosed herein. Preferably the imaging agent has reached a stable, maintainable signal level in the target region and, even more preferably, has reached a saturation point wherein the signal level or strength will not increase without the further administration of contrast agent. For the purposes of the present example, the microbubbles in the target region or tissue may be disrupted by exposing them to a rapid ultrasonic scan at a power level sufficient to depress the signal strength of the imaging agent by a discernible amount. It will be appreciated that the disruptive pulse may comprise diagnostic ultrasonic energy or therapeutic ultrasonic energy provide the desired signal reduction is obtained. Preferably, the signal strength or level in the target region will be reduced at least 5% below the measurable signal prior to the disruption scan. More preferably the signal level will be reduced 10%, 20%, 30%, 40% or 50% below that provided by the same amount of undisrupted contrast agent. In particularly preferred embodiments the post disruption signal level will be 60%, 70%, 75%, 80% or even 90% less than the pre disruption level. These decreases in signal strength correspond to disruption of the contrast agent microbubbles.

In particular, it appears that disruption of the microbubbles causes them to dissipate with a corresponding linear decrease in signal from the contrast agent proportional to the percentage of microbubbles that were disrupted. Accordingly, in selected embodiments the power level (taking into account the exposure time) may be sufficient to disrupt more than 10% of the microbubbles in the target region. Preferably, the power level is sufficient to disrupt more than 50% of the microbubbles in the target region or tissue. More preferably, the power level is sufficient to disrupt more than 90% of the microbubbles in the target region or tissue.

It will be appreciated that use of the term "frame" as in baseline frame or maximum signal frame will be held to mean the measurement of signal level over a short discrete interval i.e. on the order of $1/60^{th}$ of a second. Over a selected area or region, the signal level may be quantified by any one of a number of methods such as determining the average signal level over the region or providing the sum of the entire signal received over the area interrogated. Those skilled in the art of digital signal processing will appreciate that several techniques are compatible with the instant invention. In any case, the "frame" will be quantified to provide a representation of the signal received and, by extension, the amount of imaging agent in the target region at a given time. It will further be appreciated that it is typically these measured and quantified levels which are processed to provide the selected values for fluid flow rate and fluid content.

In preferred embodiments the disruptive energy is focused only on the tissue of the target region and not on laterally adjacent regions from which blood travels (along with intact imaging agent) to perfuse the target region. Those skilled in the art will appreciate that magnetic resonance, ultrasound and other imaging devices may be directed or focused on relatively small areas. Preferably the target region (as measured on the surface of the object or body) is less than 36 square inches. More preferably, the target region is of a minimum size to provide the necessary data, i.e. just large enough to provide an imagable frame with a quantifiable signal. It is also desirable that the angle at which the energy enters the tissue is selected so that adjacent blood-flow source regions are located laterally to, and not in front of or behind the target tissue.

In practicing the present invention, the detection parameters may be adjusted to provide the maximum contrast and/or resolution. For example, ultrasound or MRI detection settings (e.g., the frequency, pulse duration, and intensity) can be varied according to the particular circumstances, with the optimal parameters for any particular situation being readily determined by one of ordinary skill in the art. Moreover, the parameters of the signal or energy (strength, duration, etc.) necessary to disrupt a significant amount of the imaging agent present in the target region or tissue may be readily determined by those of skill in the art. Preferably, when using an ultrasound imaging agent, the power level of the ultrasonic scan is within the diagnostic range. For example, the target region or tissue may be scanned at a rate of 30 or 60 frames per second at a power ranging from the minimum detection level to a level limited only by current medical practice and the sensitivity of the tissue in the target region. More specific illustration of the range of acceptable power levels are provided by the prophetic examples set forth herein.

As explained above, it is preferable that there is a pause for some preselected period following disruption of the imaging agent and reduction of the signal strength. For example, when using an ultrasound imaging agent and ultrasonic power to effect disruption and interrogation, a pause of 0.1 second following the disruptive scan may be desirable. However, it will be appreciated that continuous interrogation or interrogation at extremely short intervals (i.e. on the order of 30, 60, 100 or more cycles per second) is within the purview of the present invention and that no pause is required following the disruptive pulse.

When using microbubble imaging agents, interrogative ultrasonic pulses may be applied to the target region or tissue over a selected period of time (continuously or at discrete intervals) with measurement of the level of the signal received after each pulse. For example, ultrasonic interrogative pulses may be applied at 0.25 seconds, 0.50 seconds, 1.0 seconds, and 2.0 seconds after the pause. As alluded to above, the signal obtained from the first pulse following the disruptive scan would include the tissue and transducer artifacts from the previous frame (i.e. the final disruptive frame or baseline frame) plus the signal resulting from intact microbubbles which have entered the target region or tissue during the pause period. The signal obtained from the final disruptive pulse may be subtracted from the signal received in the subsequent interrogative pulses to remove the signal resulting from tissue and transducer artifacts, thereby yielding the signal level resulting from the influx of intact microbubbles into the target region or tissue during the intervening period. Alternatively, the signal level in the target region could be "reset" by disrupting the microbubble imaging agent present in the target region prior to measuring the signal level after the predetermined interval. The disruption may be the result of a separate energy pulse or the previous interrogative signal. In either case, the signal levels obtained from the interrogative pulse or pulses following the disruptive signal permit the rate of increase in microbubble levels per unit time to be calculated for the target region or tissue.

Preferably, at least one interrogative pulse is delivered when the target region is maximally occupied by imaging agent. For example, an interrogative pulse may be delivered at 5, 10, 15, 20 or 25 seconds after the end of the disruptive pulse to determine the highest signal level and establish the maximum signal frame for the target region. Other periods may similarly be appropriate depending on the perfusion rate. Alternatively, determination of the maximum signal level may be accomplished prior to disruption of the imaging agent. For the purpose of enhancing the accuracy of the measurement and it is preferable that the interval between the disruptive pulse and determination of the maximum signal level be relatively short in comparison to the absolute half life of the selected imaging agent; e.g., less than 50%, 20%, 10%, or 5% of the agent half life. The term "half life" is used herein in its normal sense to designate the period it takes for the signal intensity to fall to one half of its maximum value.

Dividing the increase in signal intensity per unit time (i.e. the different interrogative frames) by the signal intensity at the maximum signal frame indirectly provides the fraction of blood exchanged per unit time (or one over the average time to replace all the blood in the tissue). This calculation normally assumes that the half life of the contrast agent in the tissue is relatively long in comparison to the measurement times, so that the decrease in signal intensity due to loss of contrast agent is negligible. However, it is important to emphasize that the present invention also contemplates adjusting the calculation for the rate of loss of contrast agent. This rate, and hence the corrective factor, can be determined empirically in each instance (e.g., by a before-and-after measurement or from known half-life data for a particular contrast agent. Alternatively, if the half life of the selected agent is not relatively long compared to the measurement intervals, the contrast agent may be administered continuously to maintain stable levels of circulating contrast agent. In any event, multiplication of the fraction of blood exchanged per unit time (as determined by the present invention) by the blood content of the tissue (in ml per cc of tissue) yields the actual perfusion rate in the target region.

The blood content of the target region or tissue may be obtained from references in the literature or by empirical measurements using techniques well known in the art. For example, values of 1.6 to 9.4 mL of blood per 100 g of myocardial mass was reported by Rodriguez et al. in *Circulation* 19,570 (1959) which is incorporated herein by reference. Values for other tissue, such as liver tissue, kidney tissue, brain tissue, etc. may be similarly obtained or derived.

Alternatively, the fluid or blood content of the tissue can be calculated by dividing the net contrast signal of the target region or tissue (the maximum signal frame minus the baseline frame) by the signal obtained from a fast moving source of pure blood, such as a large artery or heart chamber, which is located approximately the same distance from the transducer as the target region. For example, if the net contrast signal obtained from the target tissue has an intensity of 10 units and the signal obtained from relatively pure, flowing blood is 100 units, then the blood content of the target region or tissue is 10%.

Where the target region of interest is the myocardial region, the natural motion of the heart can be canceled out by synchronizing the images to be quantified with an EKG and quantifying the undisrupted periods before the frame to be measured. In other words the maximum signal frame may be established prior to disruption and the baseline frame, interrogation frames and maximum signal frame are all produced during the same period of the heartbeat. This may involve gating the starting point of the undisrupted period to the heartbeat before the interrogative frame.

When using ultrasound to practice the invention, suitable commercial contrast agents (either available or under development) include Imagent, Alliance Pharmaceutical Corp., San Diego, Calif.; Albunex and Optison, both by Molecular Biosystems, Inc., San Diego, Calif.; Echogen and QW7437 both by Sonus Pharmaceuticals Bothell, Wash.; Levovist, Echovist and Sonovist, all by Schering AG, Berlin, Germany; Aerosomes-DMP115, by ImaRx Pharmaceuticals, Tucson, Ariz.; BR1 and BR14, both by Bracco International B.V., Amsterdam, NL; Qantison and Quantison Depot, both by Andaris, Ltd. Nottingham, GB; and NC100100, Nycomed Imaging AS, Oslo, Norway. Contrast agents and methods of forming contrast agents usable in the present invention are disclosed in U.S. Pat. Nos. 4,957,656, 5,141,738, 4,657,756, 5,558,094, 5,393,524, 5,558,854, 5,573,751, 5,558,853, 5,595,723, 5,558,855, 5,409,688, 5,567,413, 5,558,856, 5,556,610, 5,578,292, 5,271,928, 5,531,980 5,562,893, 4,572,203, 4,844,882, 5,552,133, 5,536,489 and 5,558,092 each of which is incorporated herein by reference. International application WO 96/40282, WO 95/01187 and WO 96/40278 further describe compatible microbubble preparations and are also incorporated herein.

As disclosed in U.S. Pat. No. 5,315,997, gases and perfluorocarbon vapors have magnetic susceptibilities substantially different from tissues and blood. Therefore, microbubble contrast agents comprising fluorinated compounds will cause changes in the local magnetic fields present in tissues and blood during MRI. As such, the aforementioned microbubble contrast agents may also be used for magnetic resonance visualization. Other exemplary MRI agents, which may be used with the present invention comprise paramagnetic and supraparamagnetic macromolecular compounds or particulates. Examples of such imaging agents are to be found in U.S. Pat. Nos. 4,675,173 and 4,849,210 each of which is incorporated herein by reference.

With respect to paramagnetic compounds, gadopentetate dimeglumine (Gd-DTPA), and transition metal ions of iron and manganese may be used in conjunction with the disclosed invention, particularly when attached to a larger molecule such as human serum albumin, dextran or polylysine. Regarding supraparamagnetic imaging agents, those comprising iron oxides may be used to provide perfusion data with the disclosed methods.

Similarly, compounds having an imagable nucleus such as $^{19}F$, $^{23}Na$ and $^{31}P$ may be particularly useful when used in conjunction with the magnetic resonance visualization techniques described herein. Useful compounds comprising an imagable nucleus are described in U.S. Pat. Nos. 5,143,715, 5,250,283, 5,116,599, 5,401,493 and 4,951,673 each of which is incorporated herein by reference. Of course, it will be appreciated that each of the useful MRI agents may be formulated and administered using techniques well known to those skilled in the art.

As indicated above, particularly preferred embodiments of the present invention comprise the use of microbubble based imaging agents. Accordingly, microbubble formulations suitable for use in the methods of the present invention are described in some detail below. However, it will be appreciated that the present methods are not limited, in any way, to the use of these particular microbubble formulations.

As used in the present description and claims, the terms "vapor" and "gas" are used interchangeably. Similarly, when referring to the tension of dissolved gas in a liquid, the more familiar term "pressure" may be used interchangeably with "tension." "Gas osmotic pressure" is more fully defined below, but in a simple approximation can be thought of as the difference between the partial pressure of a gas inside a microbubble and the pressure or tension of that gas (either in a gas phase or dissolved in a liquid phase) outside of the microbubble, when the microbubble membrane is permeable to the gas. More precisely, it relates to differences in gas diffusion rates across a membrane. The term "membrane" is used to refer to the material surrounding or defining a microbubble, whether it be a surfactant, another film forming liquid, or a solid or semisolid shell. "Microbubbles" are considered to be bubbles having a diameter between about 0.5 and 300 μm, preferably having a diameter no more than about 200, 100, or 50 μm, and for intravascular use, preferably not more than about 10, 8, 7, 6, or 5 μm (measured as average number weighted diameter of the microbubble composition). When referring to a "gas," it will be understood that mixtures of gases together having the requisite property fall within the definition, except where the context otherwise requires. A "vapor," on the other hand, is the gaseous phase of a material that is a liquid at ambient temperature and pressure, but that has an appreciable vapor pressure at the relevant temperature, e.g., body temperature.

In a particularly preferred embodiment of the present invention, the rate of blood flow through a target region or tissue is determined using harmonic ultrasound imaging with specially designed microbubbles as ultrasound contrast enhancement agents. By optimizing the ability of these gas bubbles to transform the frequency of the ultrasonic radiation to which they are subjected (the fundamental), imaging is enhanced. Although harmonic ultrasound imaging is particularly preferred for use in the disclosed methods and systems, other types of ultrasound imaging such as grey scale, doppler and color doppler are also compatible and within the purview of the instant invention.

As will be appreciated by those skilled in the art, when a gas bubble is exposed to high pressure amplitude ultrasound or is exposed to low amplitude exciting ultrasound energy near the resonant frequency of the bubble, it acts in a nonlinear fashion. That is, the change in bubble volume is no longer proportional to the change in pressure of its surroundings. This nonlinear behavior generates components of the reradiated ultrasound energy that are at frequencies other than the exciting frequency. These harmonics at frequencies both above and below the incident frequency are the result of the mechanics of motion for the system and may be used to provide the signals comprising the interrogative frames.

To detect the reradiated ultrasound energy generated by the microbubbles, the present invention makes use of a modified conventional ultrasound scanner system or commercially available harmonic imaging systems. These systems are able to detect or select one or more of the new frequencies, or harmonics, radiated by the microbubbles for production of the ultrasound image. In other words, it detects a frequency different from the emitted frequency. Equipment suitable for harmonic ultrasound imaging is disclosed in Williams et al., WO 91/15999. Many conventional ultrasound imaging devices, however, utilize transducers capable of broad bandwidth operation, and the outgoing waveform sent to the transducer is software controlled. For this reason, reprogramming to emit a waveform different from the one detected is well within the level of skill in the art.

Regardless of the imaging agent is selected, small, nontoxic doses can be administered in a peripheral vein or lymph vessel and used to determine fluid flow rates in a wide variety of target regions or tissues. Cavities or areas within a body into which microbubbles can be introduced can be imaged, and any fluid flow therein detected and quantified, according to the method of the present invention. Thus, the present invention provides means for determining fluid flow in regions previously considered inaccessible.

As previously indicated, it is not essential that the fluid whose flow rate is to be measured be located in an organic tissue. Rather, the method of the present invention can be used to determine the flow rate of any solution into which the contrast agent can be introduced, so long as the material surrounding the contrast agent is permeable to the treatments necessary to disrupt and detect the contrast agent. Where the contrast agent comprises microbubbles adapted for returning an ultrasonic signal at a frequency different than that emitted from the transducer, it is preferable that the material in which the microbubbles are located does not itself resonate in a manner which obscures the selected harmonic of the microbubbles and does not hinder the resonance of the microbubbles.

In embodiments in which microbubbles are adapted for returning an ultrasonic signal at a frequency different from that emitted by the transducer, one or more received frequencies, different from that of the frequency originally transmitted, may be measured. Preferably, the same frequency or frequencies are monitored for generating both the interrogation, baseline and maximum signal frames. Of course, it will be appreciated that the disruption signal may be at any frequency that provides the desired reduction in signal. In preferred embodiments employing harmonic imaging agents, several different frequencies different from that of the exciting frequency can be detected and processed to provide the desired values.

As with the other embodiments (i.e. those employing grey scale), the received frequency or frequencies can be processed by a variety of methods well known to one of ordinary skill in the art. These include, for example, making the receiving transducer selective toward the desired harmonic or harmonics so that it ignores the fundamental, or by using software or hardware filters to separate or isolate the various frequencies. Similarly, the signals may be processed to provide doppler images or other representations of the target region.

While microbubbles have been shown to be efficient ultrasound scatterers and are extremely useful in the present invention, one practical drawback is the short lifetime of the small (typically less than 5 microns diameter) bubbles required to pass through capillaries in suspension. Although several advancements in recent years have increased the lifetime of microbubbles, those imaging agents having relatively longer lifetimes will allow more effective determination of the rate of fluid flow. Accordingly, the microbubbles utilized in the present methods should have a lifetime sufficient to enable them to persist for the time period during which ultrasound measurements are taken.

Short microbubble lifetime is caused by the increased gas pressure inside the bubble, which results from the surface tension forces acting on the bubble. This elevated internal pressure increases as the diameter of the bubble is reduced. The increased internal gas pressure forces the gas inside the bubble to dissolve, resulting in bubble collapse as the gas is forced into solution. The LaPlace equation, $\Delta P = 2\gamma/r$, (where $\Delta P$ is the increased gas pressure inside the bubble, $\gamma$ is the surface tension of the bubble film, and r is the radius of the bubble) describes the pressure exerted on a gas bubble by the surrounding bubble surface or film. The LaPlace pressure is inversely proportional to the bubble radius; thus, as the bubble shrinks, the LaPlace pressure increases, increasing the rate of diffusion of gas out of the bubble and the rate of bubble shrinkage.

Gases and gas vapor mixtures which can exert a gas osmotic pressure opposing the LaPlace pressure can greatly retard the collapse of these small diameter bubbles. The disclosed invention includes use of microbubbles comprising a primary modifier gas or mixture of gases that dilutes an osmotic agent comprising a gas or vapor to a partial pressure less than the osmotic agent's vapor pressure. The osmotic agent or agents are generally relatively hydrophobic and relatively bubble membrane impermeable and also further possess the ability to develop gas osmotic pressures greater than 75 or 100 Torr at a relatively low vapor pressure. These osmotic agent or agents act to regulate the osmotic pressure within the bubble. Through regulating the osmotic pressure of the bubble, the osmotic agent (defined herein as a single or mixture of chemical entities) exerts pressure within the bubble, aiding in preventing collapse of the bubble.

As suggested above, fluorocarbon or fluorinated gases or vapors are particularly preferred as osmotic or stabilizing agents. The term fluorocarbon is used herein in its broadest sense and includes fully fluorinated compounds (perfluorocarbons) as well as partially fluorinated hydrocarbon materials (fluorochemicals or fluorinated compounds), including unsubstituted chains or those substituted with another halogen such as Br, Cl, or F or another substituent, such as O, OH, S, NO, and the like. For example, sulfur hexafluoride would be considered a fluorocarbon gas for the purposes of the present invention and may be used to provide stabilized microbubble preparations in accordance with the teachings herein. In selected embodiments, microbubbles useful with the present invention may contain materials that can change state from a gas to a liquid or solid at body temperature, (generally from about 35.5° C. to about 40° C.), and at useful pressures (generally about 1–2 atm). Similarly, fluorocarbons or other compounds that are not gases at room or body temperature can be used, provided that they have sufficient vapor pressure, preferably at least about 10–20 Torr, and more preferably 30, 40, 50 or 100 Torr at body temperature, or more preferably at least about 150 or 200 Torr.

In particular, substances possessing suitable solubility and/or vapor pressure criteria for the formation of microbubbles in accordance with the invention include fluoroheptane, fluorocycloheptane fluoromethylcycloheptane, fluorohexane, fluorocyclohexane, fluoropentane, fluorocyclopentane, fluoromethylcyclopentane, fluorodimethylcyclopentanes, fluoromethylcyclobutane, fluorodimethylcyclobutane, fluorotrimethylcyclobutane, fluorobutane, fluorocyclobutane, fluoropropane, fluoroethers, fluoropolyethers and fluorotriethylamines. Particularly preferred embodiments of the present invention employ microbubbles comprising perfluorohexane, perfluoropentane, perfluorobutane, perfluoropropane and sulfur hexafluoride. Other useful gases or vapors comprise sulfur hexafluoride, Freon 113, methylene chloride, Freon 12 (dichlorodifluoromethane), Freon 11 (trichloromonofluoromethane), butane, pentane, hexane, propane, methane, ethane and the like.

Whichever osmotic agent or agents are ultimately selected, it will be appreciated that microbubbles comprising mixtures of gases and/or vapors may be used with the disclosed methods as can microbubbles comprising pure gases. For example, both mixtures of fluorocarbon gases (i.e. fluorohexane and fluorobutane) and fluorocarbon gases mixed with nonfluorocarbon compounds (i.e. fluoropentane and nitrogen) can form particularly stable microbubbles. It will further be appreciated that several types of gas or vapor are compatible with either microbubble configuration, i.e. they are useful as a component of a mixture or in a pure state.

Regarding the instant invention, mixtures of gases and/or vapors may be used to form particularly long lasting microbubbles. This is because bubbles of a primary modifier gas such as air or nitrogen (including fluorocarbon gases) saturated with a selected perfluorocarbon osmotic agent can grow rather than shrink when exposed to air dissolved in a liquid due to the osmotic pressure exerted by the perfluorocarbon gas or vapor. Preferably, the osmotic agent is relatively impermeable to the bubble film and thus remains inside the bubble. Air or other gases inside the bubble are diluted by the perfluorocarbon, which acts to slow the air diffusion flux out of the bubble. This gas osmotic pressure is proportional to the concentration gradient of the perfluorocarbon vapor across the bubble film, the concentration of air surrounding the bubble, and the ratio of the bubble film permeability to air and to perfluorocarbon.

In order to stabilize microbubbles in this fashion and provide desirable harmonic characteristics, the osmotic agent is preferably present in the gas phase of the bubble at a mole fraction concentration of greater than approximately 2%, and more preferably at about 5%, 10%, 25%, 50%, or 100%. The vapor inside the bubble is preferably near saturation under the conditions of examination, preferably at least about 50%, 75% or 100% of the saturation concentration. Thus, for microbubbles used for imaging in a human, the liquid phase of the vapor in the bubble must have a vapor pressure at 37° C. greater than 2% of the pressure inside the bubble (one atmosphere plus the blood pressure of the human being examined plus the pressure caused by the surface tension of the bubble, the LaPlace pressure). This total pressure for 3 micron bubbles could reach 1.5 bar and thus requires the liquid phase of the vapor in the bubble to have a vapor pressure at 37° C. greater than approximately 23 torr. The liquid phase of the vapor should also have a low solubility in water, preferably less than 1% wt./wt.

It will be appreciated that one of ordinary skill in the art can readily determine other compounds that would perform suitably that do not meet both the solubility and vapor pressure criteria, described above. Rather, it will be understood that certain compounds can be considered outside the preferred range in either solubility or vapor pressure, if such compounds compensate for the aberration in the other category and provide a superior insolubility in water or high vapor pressure or affinity to dissolve in the surfactant used.

It should also be noted that for medical uses, the selected gases or vapors should be biocompatible or not be physiologically deleterious. Ultimately, the microbubbles containing the gas phase will decay and the gas phase will be released into the blood either as a dissolved gas or as submicron droplets of the condensed liquid. It will be understood that gases will primarily be removed from the body through lung respiration or through a combination of respiration and other metabolic pathways in the reticuloendothelial system.

The external, continuous liquid phase in which the bubble resides typically includes a surfactant or foaming agent. As discussed above, surfactants for use in microbubbles compatible with the present invention include any compound or composition that aids in the formation and maintenance of the bubble membrane by forming a layer at the interface between the phases, and having the criteria discussed above. The foaming agent or surfactant may comprise a single compound or any combination of compounds, such as in the case of co-surfactants.

It will be appreciated that a wide range of surfactants can be used. Indeed, virtually any surfactant or foaming agent (including those still to be developed) capable of facilitating formation of the microbubbles and having the properties discussed above can be used. The optimum surfactant or foaming agent or combination thereof for a given application can be determined through empirical studies that do not require undue experimentation. Consequently, one formulating microbubbles for use in the invention may choose the surfactant or foaming agents or combination thereof based upon such properties as biocompatibility, solubility of gas phase in surfactant, and optionally, non-Newtonian behavior.

When a bubble is formed employing a non-Newtonian surfactant, its surface tension, and therefore its internal pressure will change as the surface area of the bubble changes in response to the exciting ultrasound pressures. This additional expansion and contraction in response to changes in surface tension leads to a more nonlinear compressibility and therefore the generation of a higher intensity of harmonics. The expanding bubble increases the surface area of the surfactant film until the rising surface tension opposes further expansion. The compressing bubble, during the high pressure part of the exciting ultrasound cycle, will reduce the bubble surface area until the surface tension abruptly decreases, limiting further compression and distorting the sinusoidal volume change waveform, causing harmonics to be generated.

Regardless of what type of imaging is to be used, preferred surfactants for use in forming microbubbles are any surfactant or mixture, hydrocarbon or fluorinated, that has a component that will change the surface tension of water by more than 5 dynes/cm when the area per molecule of surfactant has changed by 10% as measured on a Langmuir film balance.

Other suitable surfactants are those surfactants with a component having a hydrophilic-lipophilic balance less than 11, preferably less than or equal to 8.

High molecular weight surfactants (e.g. over 1,000) diffuse slowly compared to the microsecond timeframe of ultrasound, and thus surfactants with a component with a molecular weight over 1,000 and capable of lowering the surface tension of water to 40 dynes/cm or lower are suitable independent of the above.

Considering diffusion, solubility and microsecond time scales, other suitable surfactants include any surfactant capable of lowering the surface tension of water to 40 dynes/cm or lower and having a CMC (critical micelle concentration) of 0.3 or lower volume fraction in water.

Specific examples of surfactants useful in the present invention include undenatured human albumin, phospholipids (e.g. phosphatidyl choline), sugar esters (e.g. sucrose stearate, sucrose distearate, sucrose tristearate), block copolymers (PLURONIC F-68, PLURONIC P-123), zonyl surfactants (e.g. FSK, FSC, FSO, FSN, FSE, FSP, FSA, FSJ, UR, TBS) fatty acids (e.g. stearic acid, oleic acid) and their salts (e.g. sodium stearate, potassium oleate).

In particularly preferred embodiments, the microbubble composition includes two or more surfactants that are selected to assist in the creation of a large number of microbubbles, and also to optimally reduce the surface tension at the gas/liquid interface of the bubbles with the liquid. It has been found especially advantageous to use a phospholipid in conjunction with a second surfactant of higher water solubility as a stabilizing surfactant combination to improve gas entrapment. For example, it has been found that the combination of a phospholipid with a polyoxyalkylene block copolymer provides excellent echogenicity and a relatively long half life.

As illustrated by these two surfactant systems, the individual components of a microbubble formulation may be selected to optimize selected characteristics in terms of the present invention. For example, microbubbles that may be disrupted yet long lasting can be formed with the appropriate surfactant-gas system. Similarly, increased harmonic generation as described above can be facilitated when a gas is selected that dissolves or is adsorbed to the hydrophobic regions of the selected surfactants. This adsorption or dissolution equilibrium is effected by the selected components as well as the partial pressure of the gas inside the bubble and thus by the total pressure inside the bubble. An increase in pressure applied by the exciting ultrasound beam will shift the equilibrium toward dissolution or adsorption in the surfactant layer, causing a volume change different from that expected from a linear system.

In such systems, suitable gases are ones that have a solubility/miscibility of their liquid forms with hexane, which is a model for the hydrophobic region of surfactants, of greater than 10% mole/mole at 37° C. For gases with a boiling point below 37° C., e.g. butane and perfluorobutane, this measurement must be carried out at elevated pressure. The adsorbing gas should be present in the bubble gas phase at a concentration of more than 2% by mole fraction of the gas mixture and preferably at about 5%, 10%, 25%, 50%, or 100%. The use of fluorinated surfactants with fluorinated gases is preferred. The liquid phase of the adsorbing gas should be relatively insoluble in water, less than 1% wt./wt. solubility/miscibility.

As alluded to previously, bubbles that are stabilized by viscous shells (e.g. denatured protein gel, U.S. Pat. No. 4,957,656 as well as those stabilized by saturated sugar solutions, U.S. Pat. Nos. 5,141,738 and 4,657,756) are also useful with the methods and systems disclosed herein. A bubble stabilized by its gas phase contents as discussed above (e.g., a material such as a highly fluorinated compound such as perfluorohexane, perfluoropentane, perfluorobutane, fluoropropane or sulfur hexafluoride) requires only a monomolecular layer (monolayer) of surfactant to make it stable in the bloodstream long enough for practical use with the present invention (see U.S. Pat. No. 5,605,673; and Quay, U.S. Pat. Nos. 5,558,854 and 5,558,855). Such bubbles are particularly useful when using harmonic techniques to monitor and quantitate fluid flow. In this respect, sucrose stearate, phospholipids and PLURONIC F-68 are examples of surfactants which be used to coat microbubbles with a monolayer and thus do not drastically inhibit the gas/vapor stabilized bubble's oscillations.

It will further be understood that other components can be included in useful microbubble formulations. For example, osmotic agents, stabilizers, chelators, buffers, viscosity modulators, air solubility modifiers, salts, and sugars can be added to fine tune the microbubble suspensions for maximum life and contrast enhancement effectiveness. Such considerations as sterility, isotonicity, and biocompatibility may govern the use of such conventional additives to injectable compositions. The use of such agents will be understood to those of ordinary skill in the art and the specific quantities, ratios, and types of agents can be determined empirically without undue experimentation.

There are a variety of methods which can be used to prepare microbubbles for use with the disclosed methods. Rehydration of spray dried hollow microspheres is preferred. Sonication is also a preferred method for the formation of microbubbles, i.e., through an ultrasound transmitting septum or by penetrating a septum with an ultrasound probe including an ultrasonically vibrating hypodermic needle. However, it will be appreciated that a variety of other techniques exist for bubble formation. For example, gas injection techniques can be used, such as venturi gas injection.

Other methods for forming microbubbles include formation of particulate microspheres through the ultrasonication of albumin or other protein as described in European Patent Application 0,359,246 by Molecular Biosystems, Inc.; the use of tensides and viscosity increasing agents as described in U.S. Pat. No. 4,446,442; lipid coated, non-liposomal, microbubbles as is described in U.S. Pat. No. 4,684,479; liposomes having entrapped gases as is described in U.S. Pat. Nos. 5,088,499 and 5,123,414; and the use of denatured albumin particulate microspheres as is described in U.S. Pat. No. 4,718,433. Each of these microbubble compositions is suitable for use with the methods of the present invention and, accordingly, the foregoing patents and applications are hereby incorporated by reference.

Sonication can be accomplished in a number of ways. For example, a vial containing a surfactant solution and gas in the headspace of the vial can be sonicated through a thin membrane. Preferably, the membrane is less than about 0.5 or 0.4 mm thick, and more preferably less than about 0.3 or even 0.2 mm thick, i.e., thinner than the wavelength of ultrasound in the material, in order to provide acceptable transmission and minimize membrane heating. The membrane can be made of materials such as rubber, Teflon, mylar, urethane, aluminized film, or any other sonically transparent synthetic or natural polymer film or film forming material. The sonication can be done by contacting or even depressing the membrane with an ultrasonic probe or with a focused ultrasound "beam." The ultrasonic probe can be disposable. In either event, the probe can be placed against or inserted through the membrane and into the liquid. Once the sonication is accomplished, the microbubble solution can be withdrawn from the vial and delivered to the patient.

Sonication can also be done within a syringe with a low power ultrasonically vibrated aspirating assembly on the syringe, similar to an inkjet printer. Also, a syringe or vial may be placed in and sonicated within a low power ultrasonic bath that focuses its energy at a point within the container.

Other types of mechanical formation of microbubbles are also contemplated. For example, bubbles can be formed with a mechanical high shear valve (or double syringe needle) and two syringes, or an aspirator assembly on a syringe. Even simple shaking may be used. The shrinking bubble techniques described herein are particularly suitable for mechanically formed bubbles, having lower energy input than sonicated bubbles. Such bubbles will typically have a diameter much larger than the ultimately desired biocompatible imaging agent, but can be made to shrink to an appropriate size by the loss of non-osmotic gases, thus concentrating the osmotic agent to near saturation.

In another method, microbubbles can be formed through the use of a liquid osmotic agent emulsion supersaturated with a modifier gas at elevated pressure introduced into a surfactant solution. This production method works similarly to the opening of soda pop, where the gas foams upon release of pressure, forming the bubbles.

In another method, bubbles can be formed similar to the foaming of shaving cream, using perfluoropentane, perfluorobutane, freon, or another like material that boils when pressure is released. Specifically, liquid in liquid emulsions may be formed that, upon the reduction of pressure, boil one of the liquids to provide a microbubble formulation suitable for injection. Such systems are described in WO 96/40282, incorporated herein by reference, which discloses the use of a syringe type mechanism for the ex vivo formation of microbubbles. Specifically, the subject application discloses the use of hypobaric methods for the activation of the dispersed phase in a gas or liquid in liquid emulsion. Essentially the preactivated formulation, which in preferred embodiments is a fluoropentane in water emulsion (such as disclosed in U.S. Pat. No. 5,707,607, incorporated herein by reference), is provided in a syringe having a plunger. As the plunger is pulled back through the application of energy, the pressure in the syringe is lowered or reduced thereby causing the gas or gas precursor dispersed phase (fluoropentane) to boil and form a microbubble imaging agent suitable for use in the present invention.

In still another method, dry void-containing particles or other structures (such as hollow spheres or honeycombs) that rapidly dissolve or hydrate, preferably in an aqueous solution, e.g., albumin, microfine sugar crystals, hollow spray dried sugar, salts, hollow surfactant spheres, dried porous polymer spheres, dried porous hyaluronic acid, or substituted hyaluronic acid spheres, or even commercially available dried lactose microspheres can be used to form microbubbles adapted for returning a signal at a frequency different from that emitted by the transducer.

For example, a spray dried surfactant solution can be formulated by atomizing a surfactant solution into a heated gas such as air, carbon dioxide, nitrogen, or the like to obtain dried 1-10 micron or larger hollow or porous spheres, which are packaged in a vial filled with an osmotic gas or a desired gas mixture as described herein. The gas will diffuse into the voids of the spheres. Diffusion can be aided by pressure or vacuum cycling. When reconstituted with a sterile solution the spheres will rapidly dissolve and leave osmotic gas stabilized bubbles in the vial. In addition, the inclusion of starch or dextrins, a sugar polyester and/or an inflating agent such as methylene chloride, 1,1,2-trichlorotrifluoroethane (Freon 113, EM Science, Gibbstown, N.J.) or perfluorohexane, will result in microbubbles with an increased in vivo half-life.

Particularly preferred starches for use in formation of microbubbles include those with a molecular weight of greater than about 500,000 daltons or a dextrose equivalency (DE) value of less than about 12. The DE value is a quantitative measurement of the degree of starch polymer hydrolysis. It is a measure of reducing power compared to a dextrose standard of 100. The higher the DE value, the greater the extent of starch hydrolysis. Such preferred starches include food grade vegetable starches of the type commercially available in the food industry, including those sold under the trademarks N-LOK and CAPSULE by National Starch and Chemical Co., (Bridgewater, N.J.); derivatized starches, such as hydroxyethyl starch (available under the trademarks HETASTARCH and HESPAN from du Pont Pharmaceuticals) (M–Hydroxyethylstarch, Ajinimoto, Tokyo, Japan). (Note that short chain starches spray dry well and can be used to produce microbubbles, but are not preferred because those with a molecular weight less than about 500,000 do not stabilize the microbubbles. However, they can be used in applications in which additional stabilization is not required.) In the alternative, a lyophilized cake of surfactant and bulking reagents produced with a fine pore structure can be placed in a vial with a sterile solution and a head spaced with an osmotic gas mixture. The solution can be frozen rapidly to produce a fine ice crystal structure and, therefore, upon lyophilization produces fine pores (voids where the ice crystals were removed).

Alternatively, any dissolvable or soluble void-forming structures may be used. In this embodiment, where the void-forming material is not made from or does not contain surfactant, both surfactant and liquid are supplied into the container with the structures and the desired gas or gases. Upon reconstitution these voids trap the osmotic gas and, with the dissolution of the solid cake, form microbubbles with the gas or gases in them.

The inclusion of the surfactants and wetting agents, salts and buffers into the shell of the microsphere allows the use of a lower surfactant concentration. As the microsphere shell is dissolving, it temporarily surrounds the microbubble formed in its interior with a layer of aqueous phase that is saturated with the surfactants, enhancing their deposition on the microbubble's surface. Thus, spray-dried surfactant containing microspheres require only locally high concentrations of surfactant, and obviate the need for a high surfactant concentration in the entire aqueous phase.

Any of the above described microbubble preparations may be administered to a vertebrate, such as a bird or a mammal, as a contrast agent for ultrasonically imaging portions of the vertebrate. Preferably, the vertebrate is a human, and the portion that is imaged is the vasculature of the vertebrate. In this embodiment, a small quantity of microbubbles (e.g., 0.1 ml/Kg based on the body weight of the vertebrate) is introduced intravascularly into the animal. Other quantities of microbubbles, such as from about 0.005 ml/Kg to about 1.0 ml/Kg, can also be used. The heart, arteries, veins, and organs rich in blood, such as liver and kidneys can be ultrasonically imaged with this technique. Alternatively, the target tissue is a solid tissue perfused by capillaries, and the method is used to determine the perfusion rate of the tissue, or to measure or visualize different perfusion rates for different portions of the tissue. This can be useful, e.g., for detecting tumors, necrotic regions, and inadequately perfused regions.

As indicated above, any imaging techniques which allow for the monitoring of the infusion of contrast agent into the target region is compatible with the teachings herein. In this regard, all forms of magnetic resonance visualization (i.e. MRI) and ultrasound imaging are useful with the disclosed methods. Specifically, ultrasound imaging including grey scale (B-mode), Doppler (including pulsed wave, color, amplitude and harmonic) and harmonic imaging are useful with the disclosed invention. Those skilled in the art will further appreciate that any of these imaging modes may be used to provide the signal levels which, upon processing, can afford the desired values for fluid flow rates and fluid content.

If one desires to use harmonic imaging (an optional embodiment of the present invention), and the ultrasound imaging machine is set to image at a particular frequency, the outgoing waveform supplied to the sonic transducer can be a numerical fraction of the imaging frequency (e.g., ½, ⅔, ⅓, and the like) or a whole number or fractional multiple of the imaging frequency (e.g., 2, 3/2, 3, 4, and the like). With any particular combination of microbubble composition and excitation frequency, certain harmonics will be dominant. The second harmonic is a common example. Those strongest harmonics are preferred for obvious reasons, although other harmonics may be selected for reasons such as preparation of multiple images or elimination of background. Moreover several frequencies, including harmonic and non harmonic frequencies or some combination thereof, may be simultaneously detected to provide the desired image. That is, in preferred embodiments any frequency other than the insonation frequency may be used to provide the desired data. Of course, those skilled in the art will appreciate that dominant harmonics can be determined by simple empirical testing of the microbubble preparation.

Regardless of which imaging mode ultimately selected, the data obtained at the different time points may be processed using techniques well known to the skilled artisan. In this respect the collected data could be stored on any medium including tape, random access memory or on a hard disk prior to analysis. For example, images could be captured and digitized from a S-VHS tape using a 256-gray level frame grabber (Data Translation DT3852, Marlboro, Mass.). Once the image data has been captured and digitized it could be analyzed according to the teachings herein using any one of a number of commercially available computer programs. For instance, the digitized images could be downloaded at TIFF files and subsequently analyzed using software such as Image PC (public domain) or Image-Pro Plus (Media Cybernetics, Silver Spring, Md.). The derived videointensities from the various time points could then be used to derive the fluid exchange rate and perfusion rate as detailed above.

The foregoing description will be more fully understood with reference to the following Examples which provide imaging agents and methods of their use that are compatible with the instant invention.

The first Example provides an imaging agent compatible with the present invention.

EXAMPLE 1

Preparation of Ultrasound Contrast Agent Through Sonication

Microbubbles with an average number weighted size of 5 microns were prepared by sonication of an isotonic aqueous phase containing 2% PLURONIC F-68 and 1% sucrose stearate as surfactants, air as a modifier gas and perfluorohexane at a concentration near saturation at 37° C.

1.3 ml of a sterile water solution containing 0.9% NaCl, 2% PLURONIC F-68 and 1% sucrose stearate was added to a 2.0 ml vial. The vial had a remaining head space of 0.7 ml initially containing air. Air saturated with perfluorohexane vapor (220 torr of perfluorohexane with 540 torr of air) at 25° C. was used to flush the headspace of the vial. The vial was sealed with a thin 0.22 mm polytetrafluoroethylene (PTFE) septum. The vial was turned horizontally, and a ⅛" (3 mm) sonication probe attached to a 50 watt sonicator model VC50, available from Sonics & Materials, was pressed gently against the septum. In this position, the septum separates the probe from the solution. Power was then applied to the probe and the solution was sonicated for 15 seconds, forming a white solution of finely divided microbubbles, having an average number weighted size of 5 microns as measured by Horiba LA-700 laser light scattering particle analyzer.

The long half-life and acoustic properties of such preparations make them particularly suitable for use in the instant invention.

EXAMPLE 2

Preparation of a Spray Dried Ultrasound Contrast Agent

One liter of each of the following solutions was prepared with water for injection: Solution A containing 4.0% w/v N-Lok vegetable starch (National Starch and Chemical Co., Bridgewater, N.J.) and 1.9% w/v sodium chloride (Mallinckrodt, St. Louis, Mo.) and Solution B containing 2.0% Superonic F-68 (Serva, Heidelberg, Germany) and 2.0% w/v Ryoto Sucrose Stearate S-1670 (Mitsubishi-Kasei Food Corp., Tokyo, Japan). Solution B was added to a high shear mixer and cooled in an ice bath. A coarse suspension of 40 ml 1,1,2-trichlorotrifluoroethane (Freon 113; EM Science, Gibbstown, N.J.) was made in the 1 liter of solution B. This suspension was emulsified using a Microfluidizer (Microfluidics Corporation, Newton, Mass.; model M-110F) at 10,000 psi, 5° C. for 5 passes. The resulting emulsion was added to solution A to produce the following formula for spray drying:

2.0% w/v m-HES hydroxyethylstarch (Ajinimoto, Tokyo, Japan)
2.0% w/v sodium chloride (Mallinckrodt)
0.87% sodium phosphate, dibasic (Mallinckrodt)
0.26% sodium phosphate, monobasic (Mallinckrodt)
1.7% w/v Superonic F-68 (Serva)
0.3% w/v Sucrose Stearate S-1670 (Mitsubishi-Kasei Food Corp.)
0.1% w/v Sucrose Stearate S-570 (Mitsubishi-Kasei Food Corp.)
4.0% w/v 1,1,2-trichlorotrifluoroethane (Freon 113; EM Science)

This emulsion was then spray dried in a Niro Atomizer Portable Spray Dryer equipped with a two fluid atomizer (Niro Atomizer, Copenhagen, Denmark) employing the following settings:

| | |
|---|---|
| hot air flow rate | 39.5 CFM |
| inlet air temp. | 255° C. |
| outlet air temp. | 109° C. |
| atomizer air flow | 110 liters/min |
| emulsion feed rate | 1 liter/hr |

The dry, hollow spherical product had a diameter between about 1 μm and about 15 μm and was collected at the cyclone separator as is standard for this dryer. Aliquots of powder (250 mg) were weighed into 10 ml tubing vials, sparged with perfluorohexane-saturated nitrogen (2 mg perfluorohexane per ml of gas) at 13° C. and sealed. The nitrogen was saturated with perfluorohexane by passing it through three perfluorohexane filled gas washing bottles immersed in a 13° C. water bath.

The vials were reconstituted for injection with 5 ml water to 400 mg of spray dried powder after inserting an 18-gauge needle as a vent to relieve pressure as the water was injected.

Again, the relatively long half-life and excellent acoustic properties of such formulations make them particularly useful for monitoring the movement of fluid as described herein.

EXAMPLE 3

Use of Spray Dried Ultrasound Contrast Agent

A 1 ml injection of the contrast agent prepared as described in Example 2 was administered to two rabbits. The rabbits were then imaged with an experimental ultrasound instrument at the University of Toronto, Sunnybrook Health Science Center, 2075 Bayview Avenue, North York, Ontario, Canada. As with several commercial instruments that are currently available, this instrument was capable of imaging in normal gray-scale and Doppler modes as well as harmonic enhanced gray-scale and Doppler modes. Images of the heart, interior vena cava, aorta, kidneys and liver were examined. Images of the rabbit were greatly enhanced when this contrast agent was injected while imaging in the harmonic enhanced modes. Small vessels were clearly visible after contrast injection, while the nonvascular clutter signals were greatly reduced. This enhancement lasted approximately 2 to 3 minutes.

This improved harmonic response and persistence are the results of a more optimally chosen non-Newtonian surfactant system. The formula demonstrated that a condensable vapor, an absorbable vapor, a non-Newtonian surfactant and a fluorocarbon vapor stabilized monolayer surfactant bubble, generate enhanced harmonics for superior in vivo imaging. In terms of the present invention such properties may be used to provide more accurate images thereby allowing for more precise quantitation of fluid flow rates.

EXAMPLE 4

Use of Sonicated Ultrasound Contrast Agent

A microbubble contrast agent is prepared by sonication as in Example 1 above except that the atmosphere in the vial prior to sonication (and therefore the gas in the microbubbles) is 100% perfluorobutane and the solution in the sonicated vial is 0.9% saline plus 3% PLURONIC. F-68 (a Newtonian water soluble surfactant that demonstrates only small changes in surface tension when the monolayer is compressed).

A rabbit is imaged as in Example 3 above after injecting 0.3 ml of this contrast agent. While the vascular persistence and harmonic generation of this preparation are not optimal, relatively higher levels of harmonic enhancement are achieved compared to air filled microbubbles, because of the ability of perfluorobutane to dissolve in or adsorb to the hydrophobic region of the PLURONIC F-68 monolayer. In part, this is because perfluorobutane has a solubility in hexane of greater than 10% mole/mole and a water solubility of less than 1% wt./wt. Additionally, the bubbles are stabilized by their gas contents and have a monolayer of surfactant.

Again such properties may allow for the more accurate quantitation of fluid flow in accordance with the teachings herein.

EXAMPLE 5

Use of Sonicated Ultrasound Contrast Agent

The surfactant system described in Example 4 is used to provide an ultrasound contrast agent comprising microbubbles containing a gas mixture of nitrogen saturated with perfluorohexane at 13° C. Rabbits are imaged as described above using the osmotically stabilized contrast agent. In addition to the adsorption and gas stabilized monolayer effects, the present formulation is particularly effective in that perfluorohexane can condense when excited, e.g., it is present in more than 2% mole fraction of the gas phase and at a concentration above 50% of its saturation concentration, is less than 1% wt./wt. soluble in water, and has a vapor pressure at 37° C. over 23 torr.

As previously alluded to, it will be appreciated that imaging agents possessing these properties are particularly useful in the present invention.

EXAMPLE 6

Use of Liquid Perfluoropentane Emulsion Ultrasound Contrast Agent Containing a Fluorinated Surfactant A perfluoropentane emulsion is prepared according to the method disclosed in Example 42 of Quay, PCT application number PCT/US94/00422. The emulsion is administered to a rabbit which is imaged as described in Example 2 above, employing harmonic enhanced modes. Upon injection, this perfluoropentane emulsion boils at the body temperature of the rabbit to form microbubbles containing perfluoropentane gas. This gas will condense under excitation as described in the foregoing disclosure, generating enhanced harmonic signals.

The solubility of perfluoropentane in water and hexane meet the criteria above for adsorption in the surfactant layer of the microbubble, generating enhanced harmonic signals. This preparation also contains Zonyl FSO surfactant, a fluorinated non-Newtonian surfactant, whose surface tension changes rapidly when the monolayer is compressed, generating enhanced harmonic signals. The ability to disrupt the microbubble formulation by the application of ultrasonic energy, thereby reducing the strength of the signal in the target region, renders it suitable for use in the present invention.

Again, the preceding example shows that fluorocarbon gas containing microbubbles possess properties that make them particularly useful with the present invention. The following Example provides yet another imaging agent that may be used as described herein.

EXAMPLE 7

Spray Drying of Phospholipid-Containing Solution for the Production of an Ultrasound Contrast Agent One liter of the following solution was prepared in water for injection: 2.0% w/v Maltrin M-100 maltodextrin (Grain Processing Corp. Muscatine, Iowa), 0.95% w/v sodium chloride (Mallinckrodt, St. Louis, Mo.), 1.0% Superonic F-68 (Serva, Heidelberg, Germany), 1.0% w/v Ryoto Sucrose Stearate S-1670 (Mitsubishi-Kasei Food Corp., Tokyo, Japan), and 0.5% Lipoid E-100-3 hydrogenated phospholipid (Lipoid, Ludwigshafen, Germany).

This solution was then spray dried in a Niro Atomizer Portable Spray Dryer equipped with a two fluid atomizer (Niro Atomizer, Copenhagen, Denmark) employing the following settings:

| | |
|---|---|
| hot air flow rate | 39.5 CFM |
| inlet air temp. | 245° C. |
| outlet air temp. | 100° C. |
| atomizer air flow | 350 liters/min |
| liquid feed rate | 1 liter/hr |

The dry, hollow spherical product had a diameter between about 1 μM and about 15 μM and was collected at the cyclone separator as is standard for this dryer. Aliquots of powder (250 mg) were weighed into 10 ml tubing vials, evacuated and sparged with perfluorohexane-saturated nitrogen at 13° C. and sealed. The nitrogen was saturated with perfluorohexane by passing it through three perfluorohexane filled gas washing bottles immersed in a 13° C. water bath.

Upon reconstitution with 5 ml of water for injection, numerous bubbles were observed by light microscopy, ranging in size from 1 to 20 microns. The fact that many approximately 1 micron bubbles could be observed for an appreciable time demonstrates the added stability gained by including a phospholipid in the formula as an additional non-Newtonian viscoelastic surfactant.

The above described microbubble preparations may be used to determine fluid flow rates and perfusion rates as described in prophetic Examples 8–14 below. Preferably, the ultrasound device is calibrated prior to measuring the fluid flow rates. Calibration of the ultrasound device may be accomplished as described in Example 8 below.

EXAMPLE 8

Calibration of An Ultrasound Device

An ACUSON XP-128 ultrasound imaging device (Acuson Corp., Mountain View, Calif.) is calibrated in arbitrary units of ultrasound power using calibration standards comprising 1:10,0000, 1:5,000, 1:2,500, 1:1250, 1:625, 1:313, 1:156, and 1:78 dilutions of IMAGENT US (Alliance Pharmaceutical Corp., San Diego, Calif.) in saline. The calibration standards are contained in thin walled polystyrene test tubes which are suspended in a water tank.

The gray level of the contrast containing regions of the recorded images are determined with a TOMTEC P-90 image analyzer (TomTec Imaging, Inc. Boulder, Colo.). The observed gray levels are plotted with respect to the concentrations of the calibration standards to obtain arbitrary units of reflected signal strength which are directly proportional to the contrast agent concentrations. For example, the strength of the signal reflected by the calibration standard having the lowest concentration of contrast agent (1:10,000) is defined as one unit of received ultrasound power and the strength of the signal reflected by the 1:5,000 dilution of contrast agent is defined as 2 units of ultrasound power.

Table 1 lists the reflected signal strength and observed gray level for each dilution of the contrast.

TABLE I

| Reflected Signal Strength (arbitrary units) | Contrast Dilution | Gray Level |
|---|---|---|
| 1 | 1:10,000 | 20 |
| 2 | 1:5,000 | 40 |
| 4 | 1:2,500 | 60 |
| 8 | 1:1,250 | 80 |
| 16 | 1:625 | 100 |
| 32 | 1:313 | 120 |
| 64 | 1:156 | 140 |
| 128 | 1:78 | 180 |

After calibrating the ultrasound device, the fraction of the blood exchanged in the target region per second may be determined as described in Example 9 immediately below.

EXAMPLE 9

Determination of the Fraction of Blood Exchanged Per Second

During an echocardiographic exam of a human with an ACUSON XP-128, calibrated as in Example 8 above, a wall motion defect is seen, possibly indicating an infarcted region of the myocardium. A bubble based contrast agent with a circulation time 10: much longer than the time required to collect the blood flow quantitation data, such as Imagent® (Alliance Pharmaceuticals, San Diego, Calif.) is injected at a dose (approximately 0.3 mg/kg) that will produce minimal attenuation in the region of interest. The heart and myocardium are observed with a 3.3 megahertz probe at 30 frames per second and a power setting of −9 dB, a power level sufficiently low to allow most of the bubbles to survive in the myocardium. After the initial bolus passes the heart chambers 20 seconds after administration, a relatively constant gray level is observed in the myocardium.

To disrupt the microbubbles and throughout the rest of the instant example, the power setting of the ACUSON is set to 0 dB, the highest setting. Video recording is started with the instrument clock visible on the screen. The ACUSON is set to trigger frames in response to the signal connected to an external trigger jack. Logic, timer circuits and an EKG monitor are connected to an external ACUSON external trigger jack and these circuits are set to supply trigger pulses at 30 pulses (and therefore 30 frames) per second until an "arming" button is depressed. The continuous application of ultrasonic power provides for the localized disruption of the microbubble imaging agent in the target region.

After activation of the "arming" button, the next R wave (part of the cardiac cycle as determined by the EKG) starts a counter and gate that allows the next 10 pulses to trigger 10 frames and then turn the pulses off until the next R wave, when the sustained high speed pulsing of the target region with ultrasonic energy resumes. The signal returned on the last pulse of the disruption phase is recorded and used to provide a baseline frame for subsequent calculations.

Application of the sustained pulsing of the target region at a constant high power and high frame rate scan substantially disrupts the microbubble contrast agent in the target region, i.e. the myocardium or a portion thereof. Following establishment of the baseline frame, ultrasound exposure pauses for approximately 0.3 seconds (heart period of 0.66 seconds minus the time for 10 frames, 0.33 seconds) to allow new unexposed microbubbles to enter the field of view before resuming the sustained high rate pulsing of ultrasonic energy. The initial pulse of ultrasound energy following the pause is used to generate an interrogative frame (still at 0 dB) with the myocardium containing the additional contrast agent brought in by the blood flow during the pause. As the heart rate of the patient is approximately 90 beats per second, the pause is approximately ½ of the cardiac cycle. The exact time of the pause may be determined by the clock reading on the screen by playing back the videotape frame by frame. Alternatively, a timer may be used to provide the exact time pause. In any event, the first frame after the pause is always obtained in the same part of the cardiac cycle.

Although contrast agent is disrupted upon the resumed application of energy, the interrogative frame already comprises the information to derive the desired values. The infusion or entry of undisrupted or intact contrast agent into the target region produces a measurably different signal than that provided by the substantially disrupted agent in the baseline frame.

The timer circuits and counter are then adjusted (automatically or manually) to give resuming pulsing after a pause one cardiac cycle long (approximately 0.7 seconds) which is twice as long as the pause used to generate the first interrogative frame. Sustained pulsing of the target region is maintained subsequent to production of the first interrogative frame thereby providing for continued disruption of the imaging agent. Once again, 10 pulses after the peak of the R wave is recorded, application of energy to the target region is halted. In this case no new baseline frame was recorded. After a pause of 1 cardiac cycle the application of power (still at 0 dB) is resumed. Again, the first pulse of power after the pause is used to generate a signal that is recorded to provide an interrogative frame (the second interrogative frame). The cycle is continued with interrogative frames being recorded after adjusting the pause to be 1.5, 2, 2.5 and 3 cardiac cycles long. A frame is then recorded after an approximate 5 second pause to determine the gray level of the myocardium (i.e. the maximum signal frame) with unexposed contrast in the entire myocardial circulation.

The frames obtained during the imaging cycles are then examined on the TOMTEC video digitizer system using grey level imaging techniques. The signal level returned from the target region, as reflected by grey scale, and the exact pause time are determined for each recorded frame. In particular, the signal level is determined for the baseline frame, the maximum signal frame and each of the individual interrogative frames. Note that all of the frames are obtained during the same part of the cardiac cycle which reduces or eliminates artifacts and improper signal levels due to the natural movement of the heart. In any event, the received power signal for each frame is then determined from the calibration plot obtained as described above. The signal levels obtained over the measured time period are tabulated in Table II.

TABLE II

| Cardiac cycles paused | Actual Paused Time (t, sec.) | Power Signal (S, units) (Frame) |
|---|---|---|
| 0 | 0.00 | 32.0 (Baseline) |
| 0.5 | 0.34 | 42.1 (Interrogative 1) |
| 1 | 0.68 | 50.4 (Interrogative 2) |

TABLE II-continued

| Cardiac cycles paused | Actual Paused Time (t, sec.) | Power Signal (S, units) (Frame) |
|---|---|---|
| 1.5 | 0.95 | 55.9 (Interrogative 3) |
| 2 | 1.35 | 62.5 (Interrogative 4) |
| 2.5 | 1.70 | 67.2 (Interrogative 5) |
| 3 | 2.03 | 70.7 (Interrogative 6) |
| 9 (approx. 5 seconds) | 5.40 | 84.8 (Maximum Signal) |

The fraction of blood in the tissue that is exchanged each second (or blood exchange rate) may be calculated by dividing the initial signal rise per unit time by the signal obtained when the target tissue is maximally occupied by contrast agent (the maximum signal level obtained in the final measurement following the pause of approximately 5 seconds):

$$[(42.1-32.0)/0.34]/(84.8-32.0)=56\%/\text{sec.}$$

Accordingly, roughly 56% of the blood in the target region is replaced, or exchanged, every second. This rate of blood exchange is fairly normal and indicates that the myocardium of the patient is healthy and receiving enough oxygen.

It will be appreciated that this method of calculation (linear fit) may be accomplished using only three measurements; i.e. those at the baseline frame, a single interrogative frame and at maximum signal frame. However, the same calculation could be made for each interrogative frame using the same baseline frame (i.e. S=32.0) or a separate baseline frame generated during each measurement cycle. In either case, the values obtained from the calculation of blood exchange over different times (normalized by dividing the measured flow by the pause time) could be averaged to give a more accurate value for the percentage of blood exchanged every second.

It will further be appreciated that the exchange rate may be determined for any flowing liquid whether it is in a large vessel such as a water pipe or principal artery or perfusing the microvascular matrix of a selected tissue.

Alternatively, the fraction of blood exchanged each second may be more accurately determined using the stirred tank dilution exponential equation as described in Example 10.

EXAMPLE 10

Determination of Blood Fraction Exchanged Per Second Using Stirred Tank Dilution Exponential Equation As the random path of small blood vessels in the tissue approximate the mixing of a stirred tank, the stirred tank dilution exponential equation (or exponential fit) can be applied. The fraction of blood in the tissue that is exchanged each second in Example 9 is more accurately calculated by fitting the power signal data to the equation:

$$S(t)=Sp(1-\exp(-tF/V))+So$$

Where S(t) is the power of the signal after each pause, t is the pause time and Sp, So and FN are fitting parameters corresponding to the signal rise after an infinite pause, the signal with continuous ultrasonic exposure (zero pause) and the fraction of the blood exchanged each second, respectively. That is, So and S(t) may be thought of as the calculated baseline frame and the calculated interrogative frame at time t. When applied to the prophetic data in Table II, the result of the exponential or least squares fit is the equation:

$$S(t)=55(1-\exp(-t0.6))+32$$

From the above equation, the calculated baseline frame signal (t=0) is 32, the calculated maximum signal frame (t=∞) has a signal level of 87 (55+32) as the exponential factor goes to 0. Using these values and solving the equation for various time points provides a flow/volume value of approximately 0.6. Therefore approximately 60% of the blood in the myocardiuim is exchanged each second as calculated using a least squares fit. This method of calculation, besides being more accurate, has the further advantage of not requiring the empirical determination of a maximum power signal to calculate the exchange rate.

Those skilled in the art will further appreciate that, due to more accurate interpretation of the data, the calculated maximum and minimum power signals and the calculated exchange rate do not correspond exactly to the values derived in Example 9. However, both methods of data interpretation provide reasonably accurate estimations of the measured exchange rate and each is clearly within the purview of the instant invention.

Whatever method of data interpretation is employed, the derived value may then be used to calculate the blood perfusion rate with respect to the target region. More specifically, the fraction of blood exchanged per second can then be used to calculate the blood perfusion rate using blood content values obtained from the literature or determined from a moving source of blood as described in Examples 11 and 12 respectively.

EXAMPLE 11

Calculation of Blood Perfusion Rate Using Blood Content Obtained From the Literature The blood perfusion rate is calculated by multiplying the fraction of the blood exchanged in each second by the blood content of the tissue. As alluded to above, measured blood volume in the myocardium ranges from approximately 1.6% to 9.4% (Rodriguez et al. *Circulation*, 19, 570) Based on these figures it appears that, on average, myocardial tissue comprises approximately 6% blood by weight. Using this value it is relatively straight forward to calculate the perfusion rate of the patient's myocardial tissue using the blood exchange rate provided by the method set forth in Example 9:

$$(0.56)(0.06)=0.034 \text{ ml blood per ml tissue per second}$$

Accordingly, the patient's myocardial tissue in the target region is receiving approximately 3.4 ml of blood per 100 ml of tissue per second. As indicated in Example 9 by the measured exchange rate, this perfusion rate is relatively high allowing the attending physician to infer that the observed tissue is well supplied with oxygenated blood and healthy. Using the blood exchange value calculated by the exponential equation set forth in Example 10 and the value for myocardial blood content derived from the published literature, the perfusion rate may be calculated as follows:

$$(0.60)(0.06)=0.036 \text{ ml blood per ml tissue per second}$$

This calculation indicates that the patient's myocardial tissue in the target region is receiving approximately 3.6 ml of blood per 100 ml of tissue per second. The slightly higher figure obtained by using the value determined by curve fitting is more accurate based on the prophetic data. However, the general agreement between the figures provided by the different methods of calculating the blood exchange rate clearly demonstrates that both are compatible with the present invention and that either may be used to provide the desired perfusion rate.

EXAMPLE 12

Calculation of Blood Perfusion Rate Using Blood Content Obtained from a Moving Source of Pure Blood In addition to the methods used in the aforementioned Examples, the perfusion rate may also be determined by comparing the signal generated by blood permeating a target region with that generated by a source of fast moving, pure blood. More particularly, the blood content of the target region is calculated by dividing the signal received after a long pause by the signal obtained from a nearby large blood vessel or the heart chamber as measured in the same frame.

Using the patient and prophetic data of Example 9, the perfusion rate of the target region may be calculated by multiplying the measured signal change over a selected period times the blood exchange rate and dividing the product by the measured signal from the fast moving blood in the same frame. The signal from the fast moving blood will essentially be at a maximum as any disrupted imaging agent that was originally in the baseline frame has been replaced by fresh contrast agent during the pause. For the patient in Example 9, the measured signal from the blood in the chamber of the heart next to the target region in the interrogative frame produced after a 5.4 second pause is 678 (S=678) power units. Conversely, the signal provided by the tissue in the target region is 84.8 (S=84.8) power units. Using the approach outlined immediately above and the calculated exchange rate from Example 9, the perfusion rate for the myocardial target region of the patient may be determined as follows:

$$(0.56)(84.8-32)/678=0.044 \text{ ml blood per ml tissue per second}$$

The method generally set forth in the instant Example may also be used with the perfusion rate determined using the exponential calculation as detailed in Example 10. Using the numbers arrived at above, the perfusion rate in the target region of the patient is calculated as follows:

$$(0.60)(55)/678=0.049 \text{ ml blood per ml tissue per second}$$

Again, the relative agreement between the different calculations illustrates that various methods may be used to calculate the desired values. As such, it will be appreciated that any method of processing the empirical data obtained using the techniques disclosed herein is compatible with present invention.

EXAMPLE 13

Determination of Exchange Rate and Perfusion Rate of Blood in the Kidney

The methods described in the preceding Examples above may also be used to determine the exchange rate andperfusion rate of blood in the kidney. In particular, the present invention may be used to determine the rate of blood exchange and perfusion in the cortex of the kidney.

A patient having impaired blood flow in a kidney is imaged using the methods of the present invention. To provide enhanced signal levels a microbubble composition comprising perfluoropentane vapor is prepared according to the techniques set forth in WO 96/40282 and administered to the patient. Specifically, an oil-in-water emulsion comprising perfluoropentane in an aqueous continuous phase (as detailed in U.S. Pat. No. 5,558,853) is provided in a syringe apparatus as described in the above-referenced patent application. As the plunger of the syringe is withdrawn, the pressure in the syringe barrel is reduced thereby forming microbubbles comprising perfluoropentane vapor. The resulting microbubble composition is then administered to the patient through intravenous injection at a dose which prevents non-circulating bubbles from appreciably accumulating in the target region during the observation period. Within a relatively short time, the signal level in the kidney target region is noticeably higher.

As described above, an ACUSON XP-128 instrument and TOMTEC video digitizer system are used to measure and process the ultrasound data obtained during the procedure. With the ACUSON set at 0 dB, 3.3 Mhz and generating 30 frames a second a prolonged series of pulses, sufficient to locally disrupt at least a portion of the microbubbles, are directed to the target region comprising all or part of the patient's kidney.

After completion of the disruption phase, the power output of the ACUSON is adjusted, preferably automatically, to a lower level of −9 dB (though still at 3.3 Mhz and 30 frames per second). A baseline frame comprising an attenuated signal level (compared to the signal prior to disruption) is recorded at the new power setting. Interrogative frames are then generated at 0.2, 0.5, 1, 1.5, 2, 3, 5, 7 and 10 seconds. Optionally, a maximum signal frame is generated at 30 seconds.

Unlike the Examples previously described, the relatively low ultrasound power is applied to the target region continuously (i.e. at 30 frames/sec) during the period that the interrogative frames are being generated. At such power settings the undisrupted microbubble contrast agent infusing into the target region is not substantially destroyed and, as shown by the increasing signal levels over time, accumulates in the kidney. Moreover, as the kidney is not actively moving like the heart, the interrogative frames do not have to be timed to coincide with a particular cycle. Accordingly, every frame generated following the established baseline frame could be used as an interrogative frame if so desired.

The fraction of blood exchanged each second is calculated as described above in Example 9. Alternatively, the exponential calculation used in Example 10 may be used to calculate the exchange rate based on the collected data. In either case, the rate of blood flow (or perfusion rate) through the kidney may be calculated using the literature value for the blood content of 8% v/v as in Example 11. Conversely, the perfusion rate may be determined using a renal artery signal of 600 power units for the moving blood reference signal as in Example 12. Based on the calculated exchange rate and/or perfusion rate, the supply of blood to the patient's kidney is accurately evaluated allowing for the implementation of appropriate therapies.

EXAMPLE 14

Use of an Ultrasound Device Capable of Directly Indicating the Blood Exchange Rate or the Perfusion Rate A patient is brought to a clinic with signs of liver failure. After being injected with a microbubble contrast agent comprising partially denatured protein microspheres filled with a fluorocarbon gas, the liver is imaged using a device as disclosed herein.

More particularly, a digital storage medium is added to an ultrasound instrument similar to the ACUSON XP-128 providing it with the capability of storing digital image frames, made up of received power signal values as obtained in monitoring procedures such as those described in Examples 9 through 13.

The device further comprises a processor or processing unit capable of performing the calculations set forth in the preceding Examples employing the techniques described above. In particular, a variety of processing units exist which would be capable of receiving and analyzing the data from the individual frames. For example, the processor may include one or more forms of memory such as EPROM, ROM, RAM, etc. that can be used to store the relevant data. The computations required to provide the desired values, preferably in real time, may be easily performed on a personal computer such as one having an Intel 80486 or similar microprocessor. Those skilled in the art will have little trouble selecting an appropriate processor, which may be in a stand alone configuration or integrated, in view of the instant disclosure. The data is preferably received from the ultrasound scanner in a digital format. Any conversions necessary to transform the scanned data into numerical form may be effected either prior to or after transmission to the processor.

In addition, the device further comprises a timer capable of accurately tracking and reporting the passage of time. Preferably, the timer will be accurate to $1/100$ of a second and able to track the passage of time for a period of hours. The timer further comprises a mechanism for signaling the end of selected periods or initiating actions after predetermined intervals. In the instant invention, the timer may be used to accurately measure the passage of time between frames or coordinate the measurements with an EKG readout.

As discussed above, the device will gather data from a patient and determine the rate of blood exchange, flow rate or other parameters associated with fluid dynamics in the body. Software is used to direct this process. In the instant Example, the software is used to control the power, frame rate, and frequency of the ultrasound scanner based on preprogrammed instructions and signals received from the timer. Here, after positioning the patient, the quantitation process is started with the continuous application of power (30 frames/sec) at 0 dB. At a preprogrammed point, the processor directs the scanner to change to a power level of −9 dB and generate a baseline frame. After saving the baseline frame data, the device then automatically generates interrogative frames of the target region (i.e. a portion of the liver) at predetermined intervals as marked by the timer. The interrogative frame data and the baseline data are then processed as described above to provide the parameters describing the flow of blood through the target region.

Those skilled in the art will appreciate that the desired values may be derived and displayed using various software structures written in any one of a number of languages including, but not limited to BASIC, C++ or FORTRAN. Moreover, the selected software may be structured so as to derive the fluid exchange rate using any of the methods previously discussed including the direct curve fitting of Example 9 or the exponential calculation described in Example 10. These derived values may then be used to automatically calculate the perfusion rate as discussed above. For the purposes of this Example, the exchange rate is determined using the disclosed exponential calculation and the perfusion rate is derived using preprogrammed tissue blood levels. In any event the derived values are then displayed, preferably on a standard video display terminal in real time.

As with the software structure, the display format is not critical to the present invention and may be selected to facilitate use of the device and allow rapid appreciation of the situation. In this respect, the desired values could be displayed numerically, graphically or some combination thereof. For example, false color could be assigned (as is done in color doppler) based on calculated flow rates or exchange rates to quickly illustrate blood dynamics in the target region. It will further be appreciated that other parameters, dealing with the patient's physiological condition or the status of the device may also be displayed. In particularly preferred embodiments the calculations are performed continuously and the displayed data and parameters are updated accordingly in real time.

Here, a touch screen feedback system is provided, allowing the user to mark or outline the tissue of interest on the screen. The device calculates the blood flow or exchange rate in the marked tissue. By sequentially marking different target regions throughout the liver and determining the blood flow rates therein, the device rapidly detects a relatively small lesion where normal blood flow is impaired. The accurate, and relatively non-invasive diagnosis of the problem, allows appropriate measures to be taken.

What is claimed is:

1. A method for determining an exchange rate for a moving fluid in a target region comprising the steps of:
   introducing undisrupted imaging agent into a moving fluid, said moving fluid being present in a target region;
   allowing undisrupted imaging agent to penetrate said target region;
   disrupting the imaging agent in the target region to provide disrupted imaging agent having a signal level less than that provided by undisrupted imaging agent;
   allowing the moving fluid to transport undisrupted imaging agent from outside the target region into the target region;
   interrogating the target region with a monitor capable of registering the signal level whereby an increase in signal level corresponding to an increase in undisrupted imaging agent is observed;
   calculating the exchange rate of moving fluid in the target region based on the observed increase in signal level;
   comparing the exchange rate of moving fluid in the target region based on the observed increase in signal levels are measured at different times to ascertain the increase in signal per unit time;
   dividing the increase in signal per unit time by a measured or derived maximum signal value to obtain the fluid exchange rate, and,
   multiplying the obtained fluid rate exchange rate by the fluid content of said target region to obtain a perfusion rate for said target region.

2. The method of claim 1 wherein said target region comprises mammalian tissue.

3. The method of claim 1 wherein said target region comprises at least a portion of a mammalian organ.

4. The method of claim 1 wherein said imaging agent comprises a composition selected from the group consisting of ultrasound contrast agents and magnetic resonance imaging agents.

5. The method of claim 1 wherein said imaging agent comprises a microbubble contrast agent.

6. The method of claim 5 wherein said microbubble contrast agent comprises a fluorocarbon gas or vapor.

7. The method of claim 6 wherein said fluorocarbon gas or vapor is selected from the group consisting of fluoroheptane, fluorocycloheptane fluoromethylcycloheptane, fluorohexane, fluorocyclohexane, fluoropentane, fluorocyclopentane, fluoromethylcyclopentane, fluorodimethylcyclopentanes, fluoromethylcyclobutane, fluorodimethylcyclobutane, fluorotrimethylcyclobutane, fluorobutane, fluorocyclobutane, fluoropropane, fluoroethers, fluoropolyethers, fluorotriethylamines and combinations thereof.

8. The method of claim 7 wherein said fluorocarbon gas or vapor is perflucropentane.

9. The method of claim 7 wherein said fluorocarbon gas or vapor is perfluorohexane.

10. The method of claim 1, wherein said interrogating step comprises emitting at least one ultrasonic pulse to measure one or more signal levels indicative of the concentration of intact microbubbles in said target region.

11. The method of claim 10 wherein said imaging agent comprises a microbubble contrast agent.

12. The method of claim 11 wherein said niicrobubble contrast agent comprises a fluorocarbon gas or vapor.

13. The method of claim 12 wherein said fluorocarbon gas or vapor is selected from the group consisting of fluoroheptane, fluorocycloheptane fluoromethylcycloheptane, fluorohexane, fluorocyclohexane, fluoropentane, fluorocyclopentane, fluoromethylcyclopentane, fluorodimethylcyclopentanes, fluoromethylcyclobutane, fluorodimethylcyclobutane, fluorotrimethylcyclobutane, fluorobutane, fluorocyclobutane, fluoropropane, fluoroethers, fluoropolyethers, fluorotriethylamines and combinations thereof.

14. The method of claim 10, wherein said signal levels are measured using a frequency different from the frequency of the emitted ultrasonic pulse.

15. The method of claim 10, wherein a plurality of ultrasonic pulses are used to measure signal levels indicative of the level of intact microbubbles in said target region.

16. The method of claim 10, wherein said disrupting step comprises applying ultrasonic energy at a power level sufficient to destroy a portion of the microbubbles.

17. The method of claim 16 wherein said disrupting step and said interrogating step use equivalent ultrasonic power levels.

18. The method of claim 16, wherein there is an unsonicated interval between the termination of said disruptive ultrasonic energy and said at least one ultrasonic interrogative pulse.

19. The method of claim 1 wherein said interrogating step comprises the use of magnetic resonance imaging.

20. The method of claim 1 wherein said calculating step comprises:
   comparing at least two signal levels indicative of the concentration of intact imaging agent in said target region wherein the signal levels are measured at different times to ascertain the increase in signal per unit time;
   dividing the increase in signal per unit time by a measured or derived maximum signal value to obtain the fluid exchange rate;
   multiplying the obtained fluid exchange rate by the fluid content of said target region to obtain a perfusion rate for said target region.

* * * * *